(12) United States Patent
Tran

(10) Patent No.: US 11,986,562 B2
(45) Date of Patent: May 21, 2024

(54) COMPOSITE MATERIALS CONTAINING STRUCTURAL POLYMERS AND PHOTOREACTIVE NITRIC OXIDE RELEASING AGENTS AND USES THEREOF FOR WOUND DRESSINGS

(71) Applicant: Marquette University, Milwaukee, WI (US)

(72) Inventor: Chieu D. Tran, Milwaukee, WI (US)

(73) Assignee: Marquette University, Milwaukee, WI (US)

( * ) Notice: Subject to any disclaimer, the term of this patent is extended or adjusted under 35 U.S.C. 154(b) by 124 days.

(21) Appl. No.: 16/387,267

(22) Filed: Apr. 17, 2019

(65) Prior Publication Data

US 2019/0240372 A1  Aug. 8, 2019

Related U.S. Application Data

(63) Continuation-in-part of application No. PCT/US2017/057134, filed on Oct. 18, 2017.

(60) Provisional application No. 62/409,617, filed on Oct. 18, 2016.

(51) Int. Cl.
| | |
|---|---|
| A61L 15/46 | (2006.01) |
| A61L 15/18 | (2006.01) |
| A61L 15/28 | (2006.01) |
| A61L 15/32 | (2006.01) |
| A61L 15/42 | (2006.01) |
| A61L 15/44 | (2006.01) |
| C08L 1/00 | (2006.01) |
| C08L 5/08 | (2006.01) |
| C08L 101/00 | (2006.01) |

(52) U.S. Cl.
CPC ............... *A61L 15/28* (2013.01); *A61L 15/18* (2013.01); *A61L 15/32* (2013.01); *A61L 15/42* (2013.01); *A61L 15/44* (2013.01); *A61L 15/46* (2013.01); *C08L 101/00* (2013.01); *A61L 2300/102* (2013.01); *A61L 2300/114* (2013.01); *A61L 2300/406* (2013.01); *A61L 2400/12* (2013.01)

(58) Field of Classification Search
CPC .......... A61L 15/28; A61L 15/18; A61L 15/32; A61L 15/42; A61L 15/44; A61L 15/46; A61L 2300/102; A61L 2300/114; A61L 2300/406; A61L 2400/12; C08L 101/00
See application file for complete search history.

(56) References Cited

U.S. PATENT DOCUMENTS

| | | | |
|---|---|---|---|
| 5,374,710 A | 12/1994 | Tsien et al. | |
| 7,122,529 B2 | 10/2006 | Ruane et al. | |
| 7,888,412 B2 | 2/2011 | Holbrey et al. | |
| 8,609,843 B2 | 12/2013 | Mascharak | |
| 2005/0232963 A1 | 10/2005 | Peplow et al. | |
| 2005/0288484 A1 | 12/2005 | Holbrey et al. | |
| 2009/0149579 A1 | 6/2009 | Ito et al. | |
| 2010/0239673 A1 | 9/2010 | Linhardt et al. | |
| 2010/0297200 A1* | 11/2010 | Schoenfisch | |
| 2012/0040901 A1 | 2/2012 | Szente et al. | |
| 2012/0184014 A1* | 7/2012 | Mascharak | |
| 2014/0027938 A1 | 1/2014 | Swatloski et al. | |
| 2016/0096931 A1 | 4/2016 | Tran | |
| 2016/0145455 A1 | 5/2016 | Otake | |
| 2016/0296655 A1 | 10/2016 | Suschek | |
| 2018/0092852 A1 | 4/2018 | Gill et al. | |
| 2019/0142001 A1 | 5/2019 | Tran | |
| 2019/0240372 A1 | 8/2019 | Tran | |

FOREIGN PATENT DOCUMENTS

| | | |
|---|---|---|
| CN | 102168323 A | 8/2011 |
| CN | 103012811 A | 4/2013 |
| JP | 2007092024 A | 4/2007 |
| KR | 20090092548 A | 9/2009 |
| RU | 2321597 C2 | 4/2008 |
| WO | 9616643 A1 | 6/1996 |
| WO | 0132308 A1 | 5/2001 |
| WO | 0209782 A1 | 2/2002 |
| WO | 2004084627 A2 | 10/2004 |
| WO | 2005000280 A2 | 1/2005 |
| WO | 2005062896 A2 | 7/2005 |
| WO | 2005098546 A2 | 10/2005 |

(Continued)

OTHER PUBLICATIONS

Ohno (Green Chemistry Communication, pp. 44-46, Published 2008) (Year: 2008).*
Eroy-Reveles (Journal of American Chemical Society, Published 2008, pp. 4447-4458) (Year: 2008).*
Iwamoto (Chemical Communication, Published May 7, 2015, pp. 9539-9542) (Year: 2015).*
Duri et al., Supramolecular Composite Materials from Cellulose, Chitosan, and Cyclodextrin: Facile Preparation and Their Selective Inclusion Complex Formation with Endocrine Disruptors, Langmuir, 2013, 29(16):5037-5049.
Eroy-Reveles et al., Near-Infrared Light Activated Release of Nitric Oxide From Designed Photoactive Manganese Nitrosyls: Strategy, Design, and Potential as NO Donors, Journal of the American Chemical Society, 2008, 130(13):4447-4458.

(Continued)

*Primary Examiner* — Alma Pipic
(74) *Attorney, Agent, or Firm* — Quarles & Brady LLP

(57) ABSTRACT

Disclosed herein are composite materials, ionic liquid compositions for preparing the composite materials, and methods for using the composite materials prepared from the ionic liquid compositions. The composite materials typically include structural polymers and nitric oxide releasing agents, and preferably photo-reactive nitric oxide releasing compounds or complexes. The composite materials may be prepared from ionic liquid compositions comprising the structural polymers and the nitric oxide releasing agent, where the ionic liquid is removed from the ionic liquid compositions to obtain the composite materials. The composite materials may be used in applications include dressing for wounds, where the nitric oxide releasing agents may be induced to release nitric oxide in order to inhibit microbial growth and promote healing.

21 Claims, 4 Drawing Sheets

(56) References Cited

FOREIGN PATENT DOCUMENTS

| | | |
|---|---|---|
| WO | 2006116126 A2 | 11/2006 |
| WO | 2007012856 A1 | 2/2007 |
| WO | 2007067866 A2 | 6/2007 |
| WO | 2008043837 A1 | 4/2008 |
| WO | 2009038735 A1 | 3/2009 |
| WO | 2009060438 A2 | 5/2009 |
| WO | 2009077749 A1 | 6/2009 |
| WO | 2009131989 A2 | 10/2009 |
| WO | 2011056545 A2 | 5/2011 |
| WO | 2011056924 A1 | 5/2011 |
| WO | 2011153409 A1 | 12/2011 |
| WO | 2014172703 A1 | 10/2014 |
| WO | 2014186702 A1 | 11/2014 |
| WO | 2017156256 A1 | 9/2017 |
| WO | 2018075614 A1 | 4/2018 |

OTHER PUBLICATIONS

Harkins et al., Chitosan-Cellulose Composite for Wound Dressing Material. Part 2. Antimicrobial Activity, Blood Absorption Ability, and Biocompatibility, Journal of Biomedical Materials Research Part B: Applied Biomaterials, 2014, 102(6):1199-1206.

Hitomi et al., Electronic Tuning of Nitric Oxide Release From Manganese Nitrosyl Complexes By Visible Light Irradiation: Enhancement of Nitric Oxide Release Efficiency by the Nitro-Substituted Quinoline Ligand, Dalton Transactions, 2014, 43(5):2161-2167.

Wamoto et al., Uncaging a Catalytic Hydrogen Peroxide Generator Through the Photo-Induced Release of Nitric Dxide From a {MnNO} 6 Complex, Chemical Communications, 2015, 51(46):9539-9542.

Jain et al., Comparison of Ciprofloxacin Hydrochloride-Loaded Protein, Lipid, and Chitosan Nanoparticles for Drug Delivery, Journal of Biomedical Materials Research Part B: Applied Biomaterials, 2008, 86(1):105-112.

Kim et al., A Platform for Nitric Oxide Delivery, Journal of Materials Chemistry B, 2014, 2(4):341-356.

Koebke et al., Does the Oxidation of Nitric Oxide by oxyMyoglobin Share an Intermediate with the metMyoglobin-Catalyzed Isomerization of Peroxynitrite?, Inorganic Chemistry, 2013, 52(13):7623-7632.

Koebke et al., Direct Monitoring of the Reaction between Photochemically Generated Nitric Oxide and *Mycobacterium tuberculosis* Truncated Hemoglobin N Wild Type and Variant Forms: An Assessment of Computational Mechanistic Predictions, Biochemistry, 2016, 55(4):686-696.

Shekhter et al., Beneficial Effect of Gaseous Nitric Oxide on the Healing of Skin Wounds, Nitric Oxide, 2005, 12(4):210-219.

Stuart et al., Emerging Applications of Stimuli-Responsive Polymer Materials, Nature Materials, 2010, 9(2):101-113.

Tran et al., Recyclable Synthesis, Characterization, and Antimicrobial Activity of Chitosan-Based Polysaccharide Composite Materials, Journal of Biomedical Materials Research Part A, 2013, 101(8):2248-2257.

Tran et al., Cellulose, Chitosan, and Keratin Composite Materials. Controlled Drug Release, Langmuir, 2015, 31(4):1516-1526.

Tran et al., One-Pot Synthesis of Biocompatible Silver Nanoparticle Composites from Cellulose and Keratin: Characterization and Antimicrobial Activity, ACS Applied Materials & Interfaces, 2016, 8(50):34791-34801.

Tran et al., Facile Synthesis, Structure, Biocompatibility and Antimicrobial Property of Gold Nanoparticle Composites from Cellulose and Keratin, Journal of Colloid and Interface Science, 2018, 510:237-245.

Welton, Room-Temperature Ionic Liquids. Solvents for Synthesis and Catalysis, Chemical Reviews, 1999, 99(8):2071-2084.

Yang et al., Nitric Oxide Based Strategies for Applications of Biomedical Devices, Biosurface and Biotribology, 2015, 1(3):177-201.

PCT International Search Report and Written Opinion, PCT/US2017/057134, dated Feb. 7, 2018, 8 pages.

Mohd et al., Dissolution of Cellulose in Ionic Liquid: A Review, In AIP Conference Proceedings, 2017, vol. 1809, No. 1, pp. 020035-1 thru 020035-13.

Ohno et al., Reaction Behavior of Cellulose in an Ionic Liquid, 1-ethyl-3-methylimidazolium chloride, Journal of Wood Science, 2013, 59(3):221-228.

European Patent Office, Extended Search Report, Application No. 17862605.7, dated May 11, 2020, 8 pages.

Sule et al., A Combination of Assays Reveals Biomass Differences in Biofilms Formed by *Escherichia coli* Mutants, Letters in Applied Microbiology, 2009, 49(3):299-304.

Sullivan, Solid-Phase Behavior of Several Long-Chain N-Paraffins, Esters, and a Ketone, Journal of Research of the National Bureau of Standards, Section A, Physics and Chemistry, 1974, 78(2): 129-141.

Swatloski et al., Dissolution of Cellulose with Ionic Liquids, Journal of the American Chemical Society, 2002, 124(18):4974-4975.

Tamargo et al., The Role of Saposin C in Gaucher Disease, Molecular Genetics and Metabolism, 2012, 106(3):257-263.

Traber et al., Burn and Smoke Inhalation Injury in Sheep Depletes Vitamin E: Kinetic Studies using Deuterated Tocopherols, Free Radical Biology & Medicine, 2007, 42(9):1421-1429.

Traber et al., $\alpha$-Tocopherol Adipose Tissue Stores are Depleted after Burn Injury in Pediatric Patients, The American Journal of Clinical Nutrition, 2010, 92(6):1378-1384.

Tran et al., Simultaneous Multispectral Imaging in the Visible and Near Infrared Region: Applications in Document Authentication and Determination of Chemical Inhomogeneity of Copolymers, Analytical Chemistry, 1998, 70(22):4701-4708.

Tran et al., Determination of Binding Constants of Cyclodextrins in Room Temperature Ionic Liquids by Near-Infrared Spectrometry, Analytical Chemistry, 2002, 74(20):5337-5341.

Tran et al., Visualizing Chemical Compositions and Kinetics of Sol-Gel by Near-Infrared Multispectral Imaging Technique, Analytical Chemistry, 2002, 74(7):1604-1610.

Tran, Infrared Multispectral Imaging: Principles and Instrumentation, Applied Spectroscopy, 2003, 38(2):133-153.

Tran et al., Chiral Ionic Liquid that Functions as Both Solvent and Chiral Selector for the Determination of Enantiomeric Compositions of Pharmaceutical Products, Analytical Chemistry, 2006, 78(4):1349-1356.

Tran et al., Development of a Universal Method Based on Ionic Liquids for Determination of Enantiomeric Compositions of Pharmaceutical Product, Ionic Liquid Applications: Pharmaceuticals, Therapeutics, and Biotechnology, American Chemical Society, 2010, Chapter 4:35-54.

Tran et al., Chitosan-Cellulose Composite Materials: Preparation, Characterization and Application for Removal of Microcystin, Journal of Hazardous Materials, 2013, 252:355-366.

Tran et al., Cellulose, Chitosan and Keratin Composite Materials, Facile and Recyclable Synthesis, Conformation and Properties, ACS Sustainable Chemistry & Engineering, 2016, 4(3):1850-1861.

Tran et al., Synthesis, Structure and Antimicrobial Property of Green Composites from Cellulose, Wool, Hair and Chicken Feather, Carbohydrate Polymers, 2016, 151:1269-1276.

Tran et al., Biocompatible Copper Oxide Nanoparticle Composites from Cellulose and Chitosan: Facile Synthesis, Unique Structure, and Antimicrobial Activity, ACS Applied Materials & Interfaces, 2017, 9(49):42503-42515.

Uddin et al., Physical and Biochemical Characterization of Chemically Treated Pollen Shells for Potential Use in Oral Delivery of Therapeutics, Journal of Pharmaceutical Sciences, 2018, 107(12):3047-3059.

Venkateswarlu et al., Surfactant-Free Green Synthesis of Fe3O4 Nanoparticles Capped with 3, 4-Dihydroxyphenethylcarbamodithioate: Stable Recyclable Magnetic Nanoparticles for the Rapid and Efficient Removal of Hg (II) Ions from Water, Dalton Transactions, 2015, 44(42):18427-18437.

Watters et al., Enzymatic Degradation of in Vitro *Staphylococcus aureus* Biofilms Supplemented with Human Plasma, Infection and Drug Resistance, 2016, 9:71-78.

Gu et al., Adsorption of Avermectins on Activated Carbon: Equilibrium, Kinetics, and UV-Shielding, Transactions of Nonferrous Metals Society of China, 2009, 19:s845-s850.

(56) References Cited

OTHER PUBLICATIONS

Weinreb et al., Long-Term Clinical Outcomes in Type 1 Gaucher Disease Following 10 Years of Imiglucerase Treatment, Journal of Inherited Metabolic Disease, 2013, 36:543-553.
Wound Source, 3M™Silvercel™Non-Adherent Antimicrobial Alginate Dressing with 3M™Easylift™Precision Technology, Copyright 2008-2023 HMP Global, Inc., Retrieved from https://www.woundsource.com/product/3m-silvercel-non-adherent-antimicrobial-alginate-dressing-easylift-precision-film-technology, 7 pages.
Wu et al., Cellulose/Soy Protein Isolate Blend Films Prepared via Room-Temperature Ionic Liquid, Industrial & Engineering Chemistry Research, 2009, 48(15):7132-7136.
Xiao et al., Dissolution and Blending of Chitosan using 1,3-Dimethylimidazolium Chloride and 1-H-3-Methylimidazolium Chloride Binary Ionic Liquid Solvent, Carbohydrate Polymers, 2011, 83(1):233-238.
Yamada et al., DNA-Cyclodextrin-Inorganic Hybrid Material for Absorbent of Various Harmful Compounds, Materials Chemistry and Physics, 2011, 126(1-2):278-283.
Zhang et al., 1-Allyl-3-Methylimidazolium Chloride Room Temperature Ionic Liquid: A New and Powerful Nonderivatizing Solvent for Cellulose, Macromolecules, 2005, 38(20):8272-8277.
Zhang et al., Antibacterial Activity of Cyclodextrins Against Bacillus Strains, Archives of Microbiology, 2008, 190:605-609.
Zhao et al., Review on Microencapsulated Phase Change Materials (MEPCMs): Fabrication, Characterization and Applications, Renewable Sustainable Energy Reviews, 2011, 15(8):3813-3832 [in two parts due to file size].
Cardinal Health, Cardinal Health™Curity™AMD Antimicrobial Woven Sponges, Copyright 2023 Cardinal Health, Retrieved from https://www.cardinalhealth.com/en/product-solutions/medical/skin-and-wound-management/traditional-wound-care/woven-dressings/curity-amd-sponges.html, 1 page.
Gopu et al., Petunidin as a Competitive Inhibitor of Acylated Homoserine Lactones in Klebsiella Pneumoniae, RSC Advances, 2016, 6(4):2592-2601.
Hamad et al., Sporopollenin Microcapsules for Microencapsulation of Living Cells, Materials Research Society Symposium Proceedings, 2013, 1499, 6 pages.
Härtig et al., Kinetics of nirS Expression (Cytochrome cd1 Nitrite Reductase) in Pseudomonas Stutzeri during the Transition from Aerobic Respiration to Denitrification: Evidence for a Denitrification-Specific Nitrate- and Nitrite-Responsive Regulatory System, Journal of Bacteriology, 1999, 181(1):161-166.
Hideno, Comparison of the Thermal Degradation Properties of Crystalline and Amorphous Cellulose, as well as Treated Lignocellulosic Biomass, BioResources, 2016, 11(3):6309-6319.
Hinze, Organized Surfactant Assemblies in Separation Science, ACS Symposium Series, American Chemical Society, 1987, Chapter 1, pp. 1-82.
Huang et al., Letter to the Editor: Cleansing of Wounds by Tap Water? An Evidenced Based Systemic Analysis, International Wound Journal, 2015, 12(4):493-494.
International Standard, Biological Evaluation of Medical Devices—Part 5: Tests for in Vitro Cytotoxicity, ISO 10993-5:2009(E), 2009, 42 pages.
Ji et al., Extraction of Keratin with Ionic Liquids from Poultry Feather, Separation and Purification Technology, 2014, 132:577-583.
Jia et al., Preparation of Copper Nanoparticles Coated Cellulose Films with Antibacterial Properties through One-Step Reduction, ACS Applied Materials & Interfaces, 2012, 4(6):2897-2902.
Johnston et al., Nanogold and Nanosilver Composites with Lignin-Containing Cellulose Fibres, Journal of Materials Science, 2012, 47:1103-1112.
Joint Trauma System Clinical Practice Guideline (JTS CPG), Burn Wound Management Under Prolonged Field Care (CPG ID:57), 2017, 20 pages.
Khait et al., Multispectral Imaging Microscope with Millisecond Time Resolution, Analytical Chemistry, 2001, 73(4):732-739.
Kitaoka et al., Adsorption of Bisphenol A by Cross-Linked β-Cyclodextrin Polymer, Journal of Inclusion Phenomena and Macrocyclic Chemistry, 2002, 44:429-431.
Konop et al., Certain Aspects of Silver and Silver Nanoparticles in Wound Care: A Minireview, Journal of Nanomaterials, 2016, 2016:1-10.
Kundu et al., Arsenic Adsorption onto Iron Oxide-Coated Cement (IOCC): Regression Analysis of Equilibrium Data with Several Isotherm Models and their Optimization, Chemical Engineering Journal, 2006, 122(1-2):93-106.
Langmuir, The Constitution and Fundamental Properties of Solids and Liquids, Part 1, Solids, Journal of the American Chemical Society, 1916, 38(11):2221-2295 [in two parts due to file size].
Li et al., The Molecular Structure of Plant Sporopollenin, Nature Plants, 2018, bioRxiv preprint doi: https://doi.org/10.1101/415612, 150 pages [in three parts due to file size].
Liebert et al., Cellulose Solvents: For Analysis, Shaping and Chemical Modification, ACS Symposium Series: American Chemical Society, 2010, 1033, 299-317.
Lipman et al., Odor Absorbing Hydrocolloid Dressings for Direct Wound Contact, Wounds, 2007, 19(5):138-146.
McDougald et al., Should we Stay or Should we go: Mechanisms and Ecological Consequences for Biofilm Dispersal, Nature Reviews Microbiology, 2012, 10(1):39-50.
Medline, SilvaSorb Silver Antimicrobial Wound Gel, Copyright 2023 Medline Industries, LP, Retrieved from https://punchout.medline.com/product/SilvaSorb-Silver-Antimicrobial-Wound-Gel/Antimicrobial-Gel/Z05-PF00181, 1 page.
Mejac et al., Visualizing the Size, Shape, Morphology, and Localized Surface Plasmon Resonance of Individual Gold Nanoshells by Near-Infrared Multispectral Imaging Microscopy, Analytical Chemistry, 2009, 81(16):6687-6694.
Mejac et al., Visualizing the Lower Critical Solution Temperature Phase Transition of Individual Poly(Nipam)-Based Hydrogel Particles using Near-Infrared Multispectral Imaging Microscopy, Analytical Chemistry, 2010, 82(5):1698-1704.
Mejac et al., Visualizing the Effect of Gold Nanocages on Absorption, Imaging and Lower Critical Solution Temperature Phase Transition of Individual Poly(NiPAM)-Based Hydrogel Particles by Near Infrared Multispectral Imaging Microscopy, Analytical Chemistry, 2011, 83(9):3520-3527.
Metcalf et al., Biofilm Delays Wound Healing: A Review of the Evidence, Burns & Trauma, 2013, 1(1):5-12.
Miller, Chemical Principles of Near-Infrared Technology, Near-Infrared Technology in the Agricultural and Food Industries, 2001, Chapter 2:19-37.
Mundargi et al., Eco-Friendly Streamlined Process for Sporopollenin Exine Capsule Extraction, Scientific Reports, 2016, 6(1):19960, pp. 1-14.
Mututuvari et al., Facile Synthesis, Characterization and Antimicrobial Activity of Cellulose-Chistosan-Hydroxyapatite Composite Material, A Potential Material for Bone Tissue Engineering, Journal of Biomedical Materials Research, Part A, 2013, 101(11):3266-3277.
Mututuvari et al., Synergistic Adsorption of Heavy Metal Ions and Organic Pollutants by Supramolecular Polysaccharide Composite Materials from Cellulose, Chitosan and Crown Ether, Journal of Hazardous Materials, 2014, 264:449-459.
Naqvi et al., Combined Efficacy of Biologically Synthesized Silver Nanoparticles and Different Antibiotics Against Multidrug-Resistant Bacteria, International Journal of Nanomedicine, 2013, 8:3187-3195.
Ngah et al., Comparison Study of Copper Ion Adsorption on Chitosan, Dowex A-1, and Zerolit 225, Journal of Applied Polymer Science, 1998, 67(6):1067-1070.
Nobile et al., Candida Albicans Biofilms and Human Disease, Annual Review of Microbiology, 2015, 69:71-92.
O'Toole et al., Initiation of Biofilm Formation in Pseudomonas Fluorescens WCS365 Proceeds via Multiple, Convergent Signaling Pathways: A Genetic Analysis, Molecular Microbiology, 1998, 28(3):449-461.
Ohno et al., Task Specific Ionic Liquids for Cellulose Technology, Chemistry Letters, 2009, 38(1):2-7.

(56) References Cited

OTHER PUBLICATIONS

Ozturk et al., Burn Wound Cooling with Tap Water: Is it Safe in Developing Countries or Not?, International Wound Journal, 2016, 13(5):1083.
Palazzo et al., Chiral Ionic Liquids Supported on Natural Sporopollenin Microcapsules, RSC Advances, 2018, 8(38):21174-21183.
Peng et al., Nanoporous Magnetic Cellulose-Chitosan Composite Microspheres: Preparation, Characterization, and Application for Cu (II) Adsorption, Industrial & Engineering Chemistry Research, 2014, 53(6):2106-2113.
Peng et al., n Alkanes Phase Change Materials and Their Microencapsulation for Thermal Energy Storage: A Critical Review, Energy & Fuels, 2018, 32(7):7262-7293 [in three parts due to file size].
Peppas et al., A Simple Equation for the Description of Solute Release III: Coupling of Diffusion and Relaxation, International Journal of Pharmaceuticals, 1989, 57(2):169-172.
Percival et al., Biofilms and Wounds: An Overview of the Evidence, Advances in Wound Care, 2015, 4(7):373-381.
Percot et al., Characterization of Shrimp Shell Deproteinization, Biomacromolecules, 2003, 4(5):1380-1385.
Petruzzi et al., Biofilm Formation and Avian Immune Response Following Experimental Acute and Chronic Avian Cholera due to Pasteurella Multocida, Veterinary Microbiology, 2018, 222:114-123.
Rabea et al., Chitosan as Antimicrobial Agent: Applications and Mode of Action, Biomacromolecules, 2003, 4 (6):1457-1465.
Raffi et al., Investigations into the Antibacterial Behavior of Copper Nanoparticles Against *Escherichia coli*, Annals of Micriobiology, 2010, 60(1):75-80.
Rebek, Jr., Introduction to the Molecular Recognition and Self-Assembly Special Feature, Proceedings of the National Academy of Sciences, 2009, 106(26):10423-10424.
Rebek, Jr., Molecular Behavior in Small Spaces, Accounts of Chemical Research, 2009, 42(10):1660-1668.
Rosewald et al., Cellulose-Chitosan-Keratin Composite Materials: Synthesis and Immunological and Antibacterial Properties, ECS Transactions, 2014, 64(4):499-505.
Rossi et al., Analysis of Protein-Ligand Interactions by Fluorescence Polarization, Nature Protocols, 2011, 6(3):365-387.
Souza et al., Study of Enzyme Replacement Therapy for Gaucher Disease: Comparative Analysis of Clinical and Laboratory Parameters at Diagnosis and After Two, Five and Ten Years of Treatment, Revista Brasileira de Hematologia e Hemoterapia, 2014, 36(5):345-350.
Su et al., Crystallization Features of Normal Alkanes in Confined Geometry, Accounts of Chemical Research, 2014, 47 (1):192-201.
Adjepong et al., The Role of Antioxidant Micronutrients in the Rate of Recovery of Burn Patients: A Systematic Review, Burns & Trauma, 2016, 4(18):1-7.
Alexander et al., Near-Infrared Multispectral Imagine Technique for Visualizing Sequences of Di-and Tripeptides Synthesized by Solid Phase Combinatorial Method, Applied Spectroscopy, 2001, 55(7):939-945.
Alshehri et al., Delivery of Ibuprofen by Natural Macroporous Sporopollenin Exine Capsules Extracted from *Phoenix dactylifera* L., European Journal of Pharmaceutical Sciences, 2016, 88:158-165.
American Burn Association, Support Funding for the Military Burn Research Program in FY19, 2018, 7 pages.
Asahi et al., Simple Observation of Streptococcus Mutans Biofilm by Scanning Electron Microscopy using Ionic Liquids, AMB Express, 2015, 5(6):1-9.
Atrian et al., An Evolutionary and Structure-Based Docking Model for Glucocerebrosidase-Saposin C and Glucocerebrosidase-Substrate Interactions: Relevance for Gaucher Disease, Proteins: Structure, Function, and Bioinformatics, 2008, 70(3):882-891.
Baptista et al., Near-Infrared Detection of Flow Injection Analysis by Acoustooptic Tunable Filter Based Spectrophotometry, Analytical Chemistry, 1996, 68(6):971-976.

Barrier et al., Viability of Plant Spore Exine Capsules from Microencapsulation, Journal of Materials Chemistry, 2011, 21(4):975-981.
Baxter et al., Improved Method for I.R. Determination of the Degree of N-Acetylation of Chitosan, International Journal of Biological Macromolecules, 1992, 14(3):166-169.
Benhabiles et al., Antibacterial Activity of Chitin, Chitosan and its Oligomers Prepared from Shrimp Shell Waste, Food Hydrocolloids, 2012, 29(1):48-56.
Berth et al., The Degree of Acetylation of Chitosans and its Effect on the Chain Conformation in Aqueous Solution, Carbohydrate Polymers, 2002, 47(1):39-51.
Bettinetti et al., Polymorphism, Pseudopolymorphism, and Amorphism of Peracetylated α-, β-, and γ-Cyclodextrins, Journal of Pharmaceutical and Biomedical Analysis, 2006, 41(4):1205-1211.
Boh et al., Microencapsulation Technology and its Applications in Building Construction Materials, RMZ—Materials and Geoenvironment, 2008, 55(3):329-344.
Bojana et al., Microencapsulation Technology and Applications in Added-Value Functional Textiles, Physical Sciences Reviews, 2016, 1(1):20150003, pp. 1-27.
Bordenave et al., Hydrophobization and Antimicrobial Activity of Chitosan and Paper-Based Packaging Material, Biomacromolecules, 2010, 11(1):88-96.
Brumshtein et al., Characterization of Gene-Activated Human Acid-Beta-Glucosidase: Crystal Structure, Glycan Composition, and Internalization into Macrophages, Glycobiology, 2010, 20(1):24-32.
Burkatovskaya et al., Use of Chitosan Bandage to Prevent Fatal Injections Developing from Highly Contaminated Wounds in Mice, Biomaterials, 2006, 27(22):4157-4164.
Cai et al., Dilute Solution Properties of Cellulose in LiOH/Urea Aqueous System, Journal of Polymer Science Part B: Polymer Physics, 2006, 44(21):3093-3101.
Chakraborty et al., Adsorption of Crystal Violet from Aqueous Solution onto NaOH-Modified Rice Husk, Carbohydrate Polymers, 2011, 86(4):1533-1541.
Cheng et al., Interplay Between Candida Albicans and the Mammalian Innate Host Defense, Infection and Immunity, 2012, 80(4):1304-1313.
Cheng et al., Synthesis and Antibacterial Effects of Aqueous Colloidal Solutions of Silver Nanoparticles using Aminocellulose as a Combined Reducing and Capping Reagent, Green Chemistry, 2013, 15(4):989-998.
Chiappe et al., Product as Reaction Solvent: An Unconventional Approach for Ionic Liquid Synthesis, Organic Process Research & Development, 2016, 20(12):2080-2084.
Chiappe et al., From Pollen Grains to Functionalized Microcapsules: A Facile Chemical Route Using Ionic Liquids, Green Chemistry, 2017, 19(4):1028-1033.
Chowdhury et al., Biosorption of Basic Green 4 from Aqueous Solution by Ananas Comosus (Pineapple) Leaf Powder, Colloids and Surfaces B: Biointerfaces, 2011, 84(2):520-527.
Cilurzo et al., Regenerated Keratin Proteins as Potential Biomaterial for Drug Delivery, Polymers for Advanced Technologies, 2013, 24(11):1025-1028.
Combat Medical, Our Process, Copyright Combat Medical 2023, Retrieved from https://combatmedical.com/our-process/, 3 pages.
Convatec, Aquacel® Family of Dressings, Copyright 2022 Convatec, Inc., Retrieved from https://www.convatec.com/advanced-wound-care/aquacel-family-of-dressings/, 4 pages.
Costerton et al., Bacterial Biofilms: A Common Cause of Persistent Infections, Science, 1999, 284 (5418):1318-1322.
Crini, Recent Developments in Polysaccharide-Based Materials Used as Adsorbents in Wastewater Treatment, Progress in Polymer Science, 2005, 30(1):38-70.
Da Roz et al., Adsorption of Chitosan on Spin-Coated Cellulose Films, Carbohydrate Polymers, 2010, 80(1):65-70.
Da Silva Ferreira et al., Green Production of Microalgae-Based Silver Chloride Nanoparticles with Antimicrobial Activity Against Pathogenic Bacteria, Enzyme and Microbial Technology, 2017, 97:114-121.
De Alvarenga, Characterization and Properties of Chitosan, Biotechnology of Biopolymers, 2011, 91:91-108.

(56) References Cited

OTHER PUBLICATIONS

Diego-Taboada et al., Protein Free Microcapsules Obtained from Plant Spores as a Model for Drug Delivery: Ibuprofen Encapsulation, Release and Taste Masking, Journal of Materials Chemistry B, 2013, 1(5):707-713.
Do et al., Phase-Change Core/Shell Structured Nanofibers Based on Eicosane/Poly(Vinylidene Fluoride) for Thermal Storage Applications, Korean Journal of Chemical Engineering, 2013, 30(7):1403-1409.
Dreve et al., Chitosan-Based Delivery Systems for Diclofenac Delivery: Preparation and Characterization, Journal of Physics: Conference Series, 2009, 182(012065), pp. 1-4.
Dubinin, The Potential Theory of Adsorption of Gases and Vapors for Adsorbents with Energetically Nonuniform Surfaces, Chemical Reviews, 1960, 60(2):235-241.
Duong et al., Nanoparticle (Star Polymer) Delivery of Nitric Oxide Effectively Negates Pseudomonas Aeruginosa Biofilm Formation, Biomacromolecules, 2014, 15(7):2583-2589.
Duri et al., Determination of Chemical Homogeneity of Fire Retardant Polymeric Nanocomposite Materials by Near-Infrared Multispectral Imaging Microscopy, Analytical Letters, 2010, 43(10-11):1780-1789.
Duri et al., Enantiomeric Selective Adsorption of Amino Acid by Polysaccharide Composite Materials, Langmuir, 2014, 30(2):642-650.
Duri et al., Composites Containing Fullernes and Polysaccharides: Green and Facile Synthesis, Biocompatibility and Antimicrobial Activity, ACS Sustainable Chemistry & Engineering, 2017, 5(6):5408-5417.
Dyab et al., Encapsulation of Erythromycin and Bacitracin Antibiotics into Natural Sporopollenin Microcapsules: Antibacterial, Cytotoxicity, In Vitro and In Vivo Release Studies for Enhanced Bioavailability, RSC Advances, 2018, 8(58):33432-33444.
Ellis, Infra-Red Absorption by the N—H Bond II in Aryl, Alkyl and Aryl-Alkyl Amines, Journal of the American Chemical Society, 1928, 50(3):685-695.
Fakayode et al., Multicomponent Analyses of Chiral Samples by Use of Regression Analysis of UV-Visible Spectra of Cyclodextrin Guest-Host Complexes, Analytical and Bioanalytical Chemistry, 2009, 394:1645-1653.
Fan et al., Extraction of Cage-Like Sporopollenin Exine Capsules from Dandelion Pollen Grains, Scientific Reports, 2018, 8(1):6565, pp. 1-11.
Fan et al., Transformation of Hard Pollen into Soft Matter, Nature Communications, 2020, 11(1):1449, pp. 1-10.
Fendt et al., Viscosities of Acetate or Chloride-Based Ionic Liquids and Some of their Mixtures with Water or Other Common Solvents, Journal of Chemical & Engineering Data, 2011, 56(1):31-34.
Fink et al., Structure Formation of Regenerated Cellulose Materials from NMMO-Solutions, Progress in Polymer Science, 2001, 26(9):1473-1524.
Fischer et al., Evidence for Kinetic Inhomogeneity in the Curing of Epoxy using the Near-Infrared Multispectral Imaging Technique, Analytical Chemistry, 1999, 71(5):953-959.
Franko et al., Thermal Lens Spectroscopy, Electronic Absorption and Luminescence Spectroscopy, Encyclopedia of Analytical Chemistry, 2010, pp. 1-32.
Gonzalez-Cruz et al., A Chemical Treatment Method for Obtaining Clean and Intact Pollen Shells of Different Species, ACS Biomaterials Science & Engineering, 2018, 4(7):2319-2329.
Giannuzzi et al., An Acute Case of Intoxication with Cyanobacteria and Cyanotoxins in Recreational Water in Salto Grande Dam, Argentina, Marine Drugs, 2011, 9(11):2164-2175.
Gonil et al., Novel Quaternized Chitosan Containing β-Cyclodextrin Moiety: Synthesis, Characterization and Antimicrobial Activity, Carbohydrate Polymers, 2011, 83(2):905-913.
Greve et al., Penetration Mechanism of Dimethyl Sulfoxide in Human and Pig Ear Skin: An ATR-FTIR and Near-FT Raman Spectroscopic In Vivo and In Vitro Study, Spectroscopy, 2008, 22(5):405-417.

Gunapala et al., 15-μm 128×128 GaAs/A1xGa1-xAs Quantum Well Infrared Photodetector Focal Plane Array Camera, IEEE Transactions on Electron Devices, 1997, 44(1):45-50.
Hale et al., Optical Constants of Water in the 200-nm to 200-μm Wavelength Region, Applied Optics, 1973, 12(3):555-563.
Han et al., Ionic Liquids in Separations, Accounts of Chemical Research, 2007, 40(11):1079-1086.
Han et al., Effective Encapsulation of Paraffin Wax in Carbon Nanotube Agglomerates for New Shape-Stabilized Phase Change Material with Enhanced Thermal Storage Capacity and Stability, Industrial & Engineering Chemistry Research, 2018, 57(39):13026-13035.
Hargreaves et al., Spectroscopic Studies of Amphotericin B Solubilized in Nanoscale Bilayer Membranes, Biochimica et Biophysica Acta (BBA)—Biomembranes, 2006, 1758(1):38-44.
Hassan et al., Removal of Boron from Industrial Wastewater by Chitosan via Chemical Precipitation, Journal of Chemical and Natural Resources Engineering, 2009, 4:1-11.
He et al., Phase-Change Characteristics and Thermal Performance of Form-Stable N-Alkanes/Silica Composite Phase Change Materials Fabricated by Sodium Silicate Precursor, Renewable Energy, 2015, 74:689-698.
Higuchi, Mechanism of Sustained-Action Medication, Theoretical Analysis of Rate of Release of Solid Drugs Dispersed in Solid Matrices, Journal of Pharmaceutical Sciences, 1963, 52(12):1145-1149.
Ibrahim et al., Comparative Isotherms Studies on Adsorptive Removal of Congo Red from Wastewater by Watermelon Rinds and Neem-Tree Leaves, Open Journal of Physical Chemistry, 2014, 4:139-146.
International Centre for Diffraction Data, Powder Diffraction FileTM (PDF®) Search, Copyright 1997-2023 JCPDS International Centre for Diffraction Data, 1 page.
Iqbal et al., In Situ Development of Self-Defensive Antibacterial Biomaterials: Phenol-g-keratin-EC Based Bio-Composites with Characteristics for Biomedical Applications, Green Chemistry, 2015, 17(7):3858-3869.
Jain et al., Raman Spectroscopy Enables Noninvasive Biochemical Characterization and Identification of the Stage of Healing of a Wound, Analytical Chemistry, 2014, 86(8):3764-3772.
Jayakumar et al., Biomaterials based on Chitin and Chitosan in Wound Dressing Applications, Biotechnology Advances, 2011, 29(3):322-337.
Jeon et al., Structures of Ionic Liquids with Different Anions Studied by Infrared Vibration Spectroscopy, The Journal of Physical Chemistry B, 2008, 112(15):4735-4740.
Jiang et al., Design and Synthesis of Magnetic Microcapsules based on n-Eicosane Core and Fe3O4/SiO2 Hybrid Shell for Dual-Functional Phase Change Materials, Applied Energy, 2014, 134:456-468.
Jorgensen et al., Antimicrobial Susceptibility Testing: A Review of General Principles and Contemporary Practices, Clinical Infectious Diseases, 2009, 49(11):1749-1755.
Kabsch et al., Dictionary of Protein Secondary Structure: Pattern Recognition of Hydrogen-Bonded and Geometrical Features, Biopolymers: Original Research on Biomolecules, 1983, 22(12):2577-2637.
Kaiser et al., Noninvasive Assessment of Burn Wound Severity Using Optical Technology: A Review of Current and Future Modalities, Burns, 2011, 37(3):377-386.
Karaman et al., Comparison of Sparse and Jack-Knife Partial Least Squares Regression Methods for Variable Selection, Chemometrics and Intelligent Laboratory Systems, 2013, 122:65-77.
Kelly et al., Colored and Functional Silver Nanoparticle-Wool Fiber Composites, ACS Applied Materials & Interfaces, 2011, 3(4):1083-1092.
Kennedy et al., Burns, Biofilm and a New Appraisal of Burn Wound Sepsis, Burn, 2010, 36(1):49-56.
Keong et al., In Vitro Models in Biocompatibility Assessment for Biomedical-Grade Chitosan Derivatives in Wound Management, International Journal of Molecular Sciences, 2009, 10(3):1300-1313.

(56) References Cited

OTHER PUBLICATIONS

Kesarkar et al., Gold Nanoparticles: Effective as Both Entry Inhibitors and Virus Neutralizing Agents Against HIV, Journal of Microbiology and Biotechnology, 2012, 2(2):276-283.

Khait et al., Time-Resolved Multispectral Imaging Spectrometer, Applied Spectroscopy, 2000, 54(12):1734-1742.

Kim et al., Interplay of Tumor Vascular Oxygenation and Tumor pO2 Observed Using Near-Infrared Spectroscopy, an Oxygen Needle Electrode, and 19F MR pO2 Mapping, Journal of Biomedical Optics, 2003, 8(1):53-62.

Konuklu et al., Nanoencapsulation of N-Alkanes with Poly(Styrene-Co-Ethylacrylate) Shells for Thermal Energy Storage, Applied Energy, 2015, 150:335-340.

Korsmeyer et al., Mechanism of Solute Release from Porous Hydrophilic Polymers, International Journal of Pharmaceuticals, 1983, 15(1):25-35.

Korte et al., Thermal Lens Spectrometric Determination of Colloidal and Ionic Silver in Water, International Journal of Thermophysics, 2011, 32:818-827.

Kumar et al., Investigation into the Interaction Between Surface-Bound Alkylamines and Gold Nanoparticles, Langmuir, 2003, 19(15):6277-6282.

Lakshmipathy et al., A Fixed Bed Column Study for the Removal of Pb2+ Ions by Watermelon Rind, Environmental Science: Water Research & Technology, 2015, 1(2):244-250.

Lakshmipathy et al., Watermelon Rind-Mediated Green Synthesis of Noble Palladium Nanoparticles: Catalytic Application, Applied Neuroscience, 2015, 5:223-228.

Lamprecht et al., The Thermal Decomposition of Copper (II) Oxalate Revisited, Thermochimica Acta, 2006, 446(1-2):91-100.

Lazary et al., Reduction of Healthcare-Associated Infections in a Long-Term Care Brain Injury Ward by Replacing Regular Linens with Biocidal Copper Oxide Impregnated Linens, International Journal of Infectious Diseases, 2014, 24:23-29.

Li et al., Purification of Chitosan by Using Sol-Gel Immobilized Pepsin Deproteinization, Carbohydrate Polymers, 2012, 88(1):206-212.

Li et al., Preparation of Regenerated Wool Keratin Films from Wool Keratin-Ionic Liquid Solutions, Journal of Applied Polymer Science, 2013, 127(4):2648-2653.

Li et al., Fabrication of Multifunctional Microcapsules Containing n-Eicosane Core and Zinc Oxide Shell for Low Temperature Energy Storage, Photocatalysis, and Antibiosis, Energy Conversion and Management, 2015, 106:873-885.

Liu et al., Biocompatible Magnetic Cellulose-Chitosan Hybrid Gel Microspheres Reconstituted from Ionic Liquids for Enzyme Immobilization, Journal of Materials Chemistry, 2012, 22(30):15085-15091.

Liu et al., Magnetic Cellulose-Chitosan Hydrogels Prepared from Ionic Liquids as Reusable Adsorbents for Removal of Heavy Metal Ions, Chemical Communications, 2012, 48(59):7350-7352.

Lokshyn et al., Nanoparticles in Antivirus Therapy, Advanced Materials Research, 2014, 854:149-155.

Mallakpour et al., A Facile, Efficient, and Green Fabrication of Nanocomposites based on L-Leucine Containing Poly(amide-imide) and PVA-Modified Ag Nanoparticles by Ultrasonic Irradiation, Colloid and Polymer Science, 2015, 293:1827-1833.

Marques et al., The Use of Near Infrared Spectroscopy and Multivariate Techniques to Differentiate *Escherichia coli* and *Salmonella enteritidis* Inoculated into Pulp Juice, Journal of Microbiological Methods, 2013, 93(2):90-94.

Mateo et al., Comparative Cytotoxicity Evaluation of Different Size Gold Nanoparticles in Human Dermal Fibroblasts, Journal of Experimental Nanoscience, 2015, 10(18):1401-1417.

McIntosh et al., Spectroscopic Analysis of Bacterial Biological Warfare Stimulants and the Effects of Environmental Conditioning on a Bacterial Spectrum, Analytical and Bioanalytical Chemistry, 2012, 404:2307-2315.

McKittrick et al., The Structure, Functions, and Mechanical Properties of Keratin, JOM, 2012, 64(4):449-468.

Mejac, Development and Applications of Ionic Liquids and Near-Infrared Multispectral Imaging Techniques, Dissertation, Marquette University, 2011, 206 pages.

Miao et al., Adsorption of Doxorubicin on Poly(Methyl Methacrylate)-Chitosan-Heparin-Coated Activated Carbon Beads, Langmuir, 2012, 28(9):4396-4403.

Ahn et al., Anti-Diabetic Effect of Watermelon (Citrullus Vulgaris Schrad) on Streptozotocin-Induced Diabetic Mice, Food Science and Biotechnology, 2011, 20(1):251-254.

Alam et al., Study on the Physico-Mechanical Properties of Photo-Cured Chitosan Films with Oligomer and Acrylate Monomer, Journal of Polymers and the Environment, 2008, 16:213-219.

Alexander et al., Near-Infrared Spectrometric Determination of Di- and Tripeptides Synthesized by a Combinatorial Solid-Phase Method, Analytical Chemistry, 2001, 73(5):1062-1067.

Alsarra, Chitosan Topical Gel Formulation in the Management of Burn Wounds, International Journal of Biological Macromolecules, 2009, 45(1):16-21.

Altiok et al., Physical, Antibacterial and Antioxidant Properties of Chitosan Films Incorporated with Thyme Oil for Potential Wound Healing Applications, Journal of Materials Science: Materials in Medicine, 2010, 21:2227-2236.

Aluigi et al., Structure and Properties of Keratin/PEO Blend Nanofibres, European Polymer Journal, 2008, 44(8):2465-2475.

Ammann et al., Detection and Differentiation of Bacterial Spores in a Mineral Matrix by Fourier Transform Infrared Spectroscopy (FTIR) and Chemometrical Data Treatment, BMC Biophysics, 2011, 4:14, pp. 1-7.

Aoki et al., Preparation of Insoluble Chitosan Beads Functionalized by Carboxymethylated Beta-Cyclodextrin, Transactions of the Materials Research Society of Japan, 2005, 30(4):1143-1146.

Aoki et al., Removal of Phenolic Compounds from Aqueous Solutions using Ionic Interaction Between Cyclodextrin Derivatives and Chitosan, Transactions of the Materials Research Society of Japan, 2010, 35(4):809-812.

Appelbaum, Microbiology of Antibiotic Resistance in *Staphylococcus aureus*, Clinical Infectious Diseases, 2007, 45(Supplement_3):S165-170.

Arrondo et al., Quantitative Studies of the Structure of Proteins in Solution by Fourier-Transform Infrared Spectroscopy, Progress in Biophysics and Molecular Biology, 1993, 59(1):23-56.

Artes-Hernandez et al., Low UV-C Illumination for Keeping Overall Quality of Fresh-Cut Watermelon, Postharvest Biology and Technology, 2010, 55(2):114-120.

Barone et al., Extrusion of Feather Keratin, Journal of Applied Polymer Science, 2006, 100(2):1432-1442.

Becherini et al., Natural Sporopollenin Microcapsules Facilitated Encapsulation of Phase Change Material into Cellulose Composites for Smart and Biocompatible Materials, ACS Applied Materials & Interfaces, 2019, 11(47):44708-44721.

Borkow, Using Copper to Improve the Well-Being of the Skin, Current Chemical Biology, 2014, 8(2):89-102.

Bowler, The 10(5) Bacterial Growth Guideline: Reassessing its Clinical Relevance in Wound Healing, Ostomy Wound Management, 2003, 49(1):44-53.

Brust et al., Synthesis of Thiol-Derivatised Gold Nanoparticles in a Two-Phase Liquid-Liquid System, Journal of the Chemical Society, Chemical Communications, 1994, 7:801-802.

Cai et al., Fabrication of Chitosan/Silk Fibroin Composite Nanofibers for Wound Dressing Applications, International Journal of Molecular Sciences, 2010, 11(9):3529-3539.

Chalmers et al., FT-IR Imaging of Polymers: An Industrial Appraisal, Vibrational Spectroscopy, 2002, 30(1):43-52.

Chan et al., A Year for Nanoscience, ACS Nano, 2014, 8(12):11901-11903.

Chang et al., Wool Powder: An Efficient Additive to Improve Mechanical and Thermal Properties of Poly(Propylene Carbonate), Composites Science and Technology, 2017, 153:119-127.

Chen et al., Complexation of Microcystins and Nodularin by Cyclodextrins in Aqueous Solution, A Potential Removal Strategy, Environmental Science & Technology, 2011, 45(6):2293-2300.

Chen et al., What Happens during Natural Protein Fibre Dissolution in Ionic Liquids, Materials, 2014, 7(9):6158-6168.

(56) References Cited

OTHER PUBLICATIONS

Chiodo et al., Glycosystems in Nanotechnology: Gold Glyconanoparticles as Carrier for Anti-HIV Prodrugs, Beilstein Journal of Organic Chemistry, 2014, 10(1):1339-1346.
Conte et al., Modifications of the Metal and Support during the Deactivation and Regeneration of Au/C Catalysts for the Hydrochlorination of Acetylene, Catalysis Science & Technology, 2013, 3:128-134.
Corliss et al., Preserving the Inflated Structure of Lyophilized Sporopollenin Exine Capsules with Polyethylene Glycol Osmolyte, Journal of Industrial and Engineering Chemistry, 2018, 61:255-264.
Costa et al., Modeling and Comparison of Dissolution Profiles, European Journal of Pharmaceutical Sciences, 2001, 13(2):123-133.
Crane et al., Monitoring the Healing of Combat Wounds using Raman Spectroscopic Mapping, Wound Repair and Regeneration, 2010, 18(4):409-416.
Crane et al., Profiling Wound Healing with Wound Effluent: Raman Spectroscopic Indicators of Infection, Proceedings of SPIE—The International Society for Optical Engineering, 2012, 8220, 9 pages.
Crane et al., Raman Spectroscopic Analysis of Combat-Related Heterotopic Ossification Development, Bone, 2013, 57(2):335-342.
Dai et al., Chitosan Acetate Bandage as a Topical Antimicrobial Dressing for Infected Burns, Antimicrobial Agents and Chemotherapy, 2009, 53(2):393-400.
De Guzman et al., Mechanical and Biological Properties of Keratose Biomaterials, Biomaterials, 2011, 32 (32):8205-8217.
Dhakal et al., Synthesis of Unconventional Materials using Chitosan and Crown Ether for Selective Removal of Precious Metal Ions, World Academy of Science, Engineering and Technology, 2009, 56:204-208.
Dhas et al., Facile Synthesis of Silver Chloride Nanoparticles using Marine Alga and its Antibacterial Efficacy, Spectrochimica Acta Part A: Molecular and Biomolecular Spectroscopy, 2014, 120:416-420.
Ditta et al., Photocatalytic Antimicrobial Activity of Thin Surface Films of TiO 2, CuO and TiO 2/CuO Dual Layers on *Escherichia coli* and Bacteriophage T4, Applied Microbiology and Biotechnology, 2008, 79:127-133 (23 pages).
Dousseau et al., Determination of the Secondary Structure Content of Proteins in Aqueous Solutions from their Amide I and Amide II Infrared Bands, Comparison between Classical and Partial Least-Squares Methods, Biochemistry, 1990, 29(37):8771-8779.
Duri et al., Polysaccharide Ecocomposite Materials: Synthesis, Characterization and Application for Removal of Pollutants and Bacteria, ECS Transactions, 2013, 50(11):573-594.
El-Hefian et al., Rheological and Morphological Studies of Chitosan/Agar/Poly (Vinyl Alcohol) Blends, Journal of Applied Sciences Research, 2010, 6(5):460-468.
El-Mekawy et al., Preparation of Chitosan Films Mixed with Superabsorbent Polymer and Evaluation of its Haemostatic and Antibacterial Activities, Journal of Applied Polymer Sciences, 2010, 116(6):3489-3496.
El-Tahlawy et al., Novel Method for Preparation of β-Cyclodextrin/Grafted Chitosan and its Application, Carbohydrate Polymers, 2006, 63(3):385-392.
Fang et al., Characterization and Evaluation of Silk Protein Hydrogels for Drug Delivery, Chemical and Pharmaceutical Bulletin, 2006, 54(2):156-162.
Fang et al., Ultrasonic Synthesis and Characterization of Polystyrene/N-Dotriacontane Composite Nanoencapsulated Phase Change Material for Thermal Energy Storage, Applied Energy, 2014, 132:551-556.
Fayaz et al., Inactivation of Microbial Infectiousness by Silver Nanoparticles-Coated Condom: A New Approach to Inhibit HIV- and HSV-Transmitted Infection, International Journal of Nanomedicine, 2012, 7:5007-5018.
Finkenstadt et al., Crystal structure of Valonia Cellulose Iβ, Macromolecules, 1998, 31(22):7776-7783.
Fischer et al., Investigation of Solid Phase Peptide Synthesis by the Near Infrared Multispectral Imaging Technique: A Detection Method for Combinatorial Chemistry, Analytical Chemistry, 1999, 71(13):2255-2261.
Frez et al., Determination of Thermal Diffusivities, Thermal Conductivities, and Sound Speeds of Room-Temperature Ionic Liquids by the Transient Grating Technique, Journal of Chemical & Engineering Data, 2006, 51(4):1250-1255.
Fujimori et al., Novel Antiviral Characteristics of Nanosized Copper (I) Iodide Particles Showing Inactivation Activity Against 2009 Pandemic H1N1 Influenza Virus, Applied and Environmental Microbiology, 2012, 78(4):951-955.
Gangadharan et al., Polymeric Microspheres Containing Silver Nanoparticles as Bactericidal Agent for Water Disinfection, Water Research, 2010, 44(18):5481-5487.
General Electric Company, Water & Process Technologies: Analytical Instruments, Sievers, Nitric Oxide Analyzer (NOA 280i), Retrieved from http://geinstruments.com/GetLibraryDoc.aspx?id=7655eda5-5862-4b93-8b3e-e57a87a8fb5c, Copyright 2008 General Electric Company, 4 pages.
Singaravelu et al., Novel Extracellular Synthesis of Monodisperse Gold Nanoparticles Using Marine Alga, Sargassum Wightii Greville, Colloids and Surfaces B: Biointerfaces, 2007, 57(1):97-101.
Sirota et al., Rotator Phases of the Normal Alkanes: An X-ray Scattering Study, The Journal of Chemical Physics, 1993, 98(7):5809-5824.
Sirota et al., Phase Transitions Among Rotator Phases of the Normal Alkanes, The Journal of Chemical Physics, 1994, 101(12):10873-10882.
Soni et al., Isolation of Sporopollenin-Like Biopolymer from Aspergillus Niger and its Characterisation, Chemical Papers, 2016, 70(12):1556-1567.
Soukup-Hein et al., Ionic Liquids in Analytical Chemistry, Annual Review of Analytical Chemistry, 2009, 2:145-168.
Sun et al., Ionic Liquids in Analytical Chemistry, Analytica Chimica Acta, 2009, 48 pages.
Sundaram et al., Classification and Structural Analysis of Live and Dead Salmonella Cells Using Fourier Transform Infrared Spectroscopy and Principle Component Analysis, Journal of Agricultural and Food Chemistry, 2012, 60(4):991-1004.
Svircev et al., Freshwater Cyanobacterial Blooms and Primary Liver Cancer Epidemiological Studies in Serbia, Journal of Environmental Science and Health, Part C, 2009, 27(1):36-55.
Takagai et al., One-Pot Synthesis with in Situ Preconcentration of Spherical Monodispersed Gold Nanoparticles using Thermoresponsive 3-(Alkyldimethylammonio)-Propyl Sulfate Zwitterionic Surfactants, Chemical Communications, 2016, 5 pages.
Tamm et al., Infrared Spectroscopy of Proteins and Peptides in Lipid Bilayers, Quarterly Reviews of Biophysics, 1997, 30(4):365-429.
Tanabe et al., Preparation and Characterization of Keratin-Chitosan Composite Film, Biomaterials, 2002, 23(3):817-825.
The Free Dictionary By Farlex, Macrocycle, Retrieved from https://web.archive.org/web/20130722182508/https://www.thefreedictionary.com/macrocycle>, Accessed on Feb. 14, 2019, 2 pages.
Tirgar et al., Removal of Airborne Hexavalent Chromium Mist using Chitosan Gel Beads as a New Control Approach, International Journal of Environmental Science & Technology, 2006, 3:305-313.
Tran et al., Principles and Analytical Applications of Acousto-Optic Tunable Filters, An Overview, Talanta, 1997, 45(2):237-248.
Tran et al., Visualizing Chemical Composition and Reaction Kinetics by the Near Infrared Multispectral Imaging Technique, Journal of Near Infrared Spectroscopy, 2000, 8(2):87-99.
Tran et al., Development and Analytical Applications of Multispectral Imaging Techniques: An Overview, Fresenius' Journal of Analytical Chemistry, 2001, 369:313-319.
Tran et al., Absorption of Water by Room-Temperature Ionic Liquids: Effect of Anions on Concentration and State of Water, Applied Spectroscopy, 2003, 57(2):152-157.
Tran, Ionic Liquids for and by Analytical Spectroscopy, Analytical Letters, 2007, 40(13):2447-2464.
Tran et al., Molecular State and Distribution of Fullerenes Entrapped in Sol-Gel Samples, The Journal of Physical Chemistry B, 2008, 112(46):14548-14559.

(56) References Cited

OTHER PUBLICATIONS

Varshosaz et al., Designing of a Thermosensitive Chitosan/Poloxamer in Situ Gel for Ocular Delivery of Ciprofloxacin, The Open Drug Delivery Journal, 2008, 2(1):61-70.
Vasconcelos et al., The Use of Keratin in Biomedical Applications, Current Drug Targets, 2013, 14(5):612-619.
Vig et al., Respiratory Syncytial Virus Inhibition by Gold and Titanium Nanoparticles, NSTI-Nanotech 2009, 2:139-142.
Vijayakumar et al., Gold Nanoparticles as an HIV Entry Inhibitor, Current HIV Research, 2012, 10(8):643-646.
Vilaplana et al., Environmental and Resources Aspects of Sustainable Biocomposites, Polymer Degradation and Stability, 2010, 95(11):2147-2161.
Vonnemann et al., Virus Inhibition Induced by Polyvalent Nanoparticles of Different Sizes, Nanoscale, 2014, 6(4):2353-2360.
Wang et al., Multivalent Glyconanoparticles with Enhanced Affinity to the Anti-Viral Lectin Cyanovirin-N, Chemical Communications, 2011, 47(30):8620-8622.
Wang et al., The Mouse Excisional Wound Splinting Model, Including Applications for Stem Cell Transplantation, Nature Protocols, 2013, 8(2):302-309.
Wang et al., Preparation of Hybrid Gold/Polymer Nanocomposites and their Application in a Controlled Antibacterial Assay, ACS Applied Materials & Interfaces, 2016, 8(42):29101-29109.
Wang et al., Construction of Cellulose/ZnO Composite Microspheres in NaOH/Zinc Nitrate Aqueous Solution Via One-Step Method, Cellulose, 2019, 26(1):557-568.
Warner et al., Perspectives on Moving Ionic Liquid Chemistry into the Solid Phase, Analytical Chemistry, 2014, 86(15):7184-7191.
Weingarten et al., Prediction of Wound Healing in Human Diabetic Foot Ulcers by Diffuse Near-Infrared Spectroscopy: A Pilot Study, Wound Repair and Regeneration, 2010, 18(2):180-185.
Westad et al., Variable Selection in Near Infrared Spectroscopy Based on Significance Testing in Partial Least Squares Regression, Journal of Near Infrared Spectroscopy, 2000, 8(2):117-124.
Westad et al., Finding Relevant Spectral Regions Between Spectroscopic Techniques by Use of Cross Model Validation and Partial Least Squares Regression, Analytica Chimica Acta, 2007, 595(1-2):323-327.
Westrick et al., A Review of Cyanobacteria and Cyanotoxins Removal/Inactivation in Drinking Water Treatment, Analytical and Bioanalytical Chemistry, 2010, 397:1705-1714.
Wikipedia, Composite Material, Retrieved from https://en.wikipedia.org/wiki/Composite_material, Accessed on Aug. 21, 2019, 1 page.
Williams et al., Dual-Band MWIR/LWIR Radiometer for Absolute Temperature Measurements, Thermosense XXVIII, SPIE, 2006, 6205, 13 pages.
Wishart et al., The 13C Chemical-Shift Index: A Simple Method for the Identification of Protein Secondary Structure using 13C Chemical-Shift Data, Journal of Biomolecular NMR, 1994, 4:171-180.
Wittaya-Areekul et al., Development and in Vitro Evaluation of Chitosan-Polysaccharides Composite Wound Dressings, International Journal of Pharmaceuticals, 2006, 313(1-2):123-128.
Wold et al., PLS-Regression: A Basic Tool of Chemometrics, Chemometrics and Intelligent Laboratory Systems, 2001, 58(2):109-130.
Wright et al., Soft-and Hard-Templated Organic Salt Nanoparticles with the Midas Touch: Gold-Shelled NanoGUMBOS, Journal of Materials Chemistry C, 2014, 11 pages.
Wright et al., Cooling of Burns: Mechanisms and Models, Burns, 2015, 41(5):882-889.
Xia et al., Recent Developments in Shape-Controlled Synthesis of Silver Nanocrystals, The Journal of Physical Chemistry C, 2012, 116(41):21647-21656.
Xie et al., Ionic Liquids as Novel Solvents for the Dissolution and Blending of Wool Keratin Fibers, Green Chemistry, 2005, 7(8):606-608.
Xu et al., Biological Evaluation of Human Hair Keratin Scaffolds for Skin Wound Repair and Regeneration, Materials Science and Engineering: C, 2013, 33(2):648-655.
Yan et al., Plankton Community Succession in Artificial Systems Subjected to Cyanobacterial Blooms Removal Using Chitosan Modified Soils, Microbial Ecology, 2009, 58:47-55.
Yang et al., Gold Nanomaterials at Work in Biomedicine, Chemical Reviews, 2015, 115(19):10410-10488.
Yilmaz et al., Enantioselective Hydrolysis of Racemic Naproxen Methyl Ester with Sol-Gel Encapsulated Lipase in the Presence of Sporopollenin, Journal of Molecular Catalysis B: Enzymatic, 2010, 62(2):162-168.
Yin et al., Study on Effective Extraction of Chicken Feather Keratins and their Films for Controlling Drug Release, Biomaterials Science, 2013, 1(5):528-536.
Cui et al., Transglutaminase-Modified Wool Keratin Film and its Potential Application in Tissue Engineering, Engineering in Life Sciences, 2013, 13(2):149-155.
Hill et al., Some Properties of Keratin Biomaterials: Kerateines, Biomaterials, 2010, 31(4):585-593.
Sando et al., Photochemical crosslinking of soluble wool keratins produces a mechanically stable biomaterial that supports cell adhesion and proliferation, Journal of Biomedical Materials Research, Part A, Dec. 2010; 95A(3):901-911.
Saul et al., Keratin Hydrogels Support the Sustained Release of Bioactive Ciprofloxacin, Journal of Biomedical Materials Research, Part A, 2011, 98(4):544-553.
Verma et al., Preparation of Scaffolds from Human Hair Proteins for Tissue-Engineering Applications, Biomedical Materials, 2008, 3(2):025007 (12 pages).
Wu et al., In Situ Synthesis of Silver-Nanoparticles/Bacterial Cellulose Composites for Slow-Released Antimicrobial Wound Dressing, Carbohydrate Polymers, 2014, 102:762-771.
Langford et al., Scherrer After Sixty Years: A Survey and Some New Results in the Determination of Crystallite Size, Journal of Applied Crystallography, 1978, 11(2):102-113.
Guzman et al., Synthesis and Antibacterial Activity of Silver Nanoparticles against Gram-Positive and Gram-Negative Bacteria, Nanomedicine: Nanotechnology, Biology, and Medicine, 2012, 8(1):37-45.
Boroumand et al., Novel Method for Synthesis of Silver Nanoparticles and their Application on Wool, Applied Surface Science, 2015, 346:477-483.
Sardar et al., Spectroscopic and Microscopic Investigation of Gold Nanoparticle Formation: Ligand and Temperature Effects on Rate and Particle Size, Journal of the American Chemical Society, 2011, 133(21):8179-8190.
Wang et al., pH-Dependent Evolution of Five-Star Gold Nanostructures: An Experimental and Computational Study, ACS Nano, 2013, 7(3):2258-2265.
Wei et al., The Synthesis of Chitosan-Based Silver Nanoparticles and their Antibacterial Activity, Carbohydrate Research, 2009, 344(17):2375-2382.
Mikhaylova et al., Preclinical Evaluation of Antimicrobial Efficacy and Biocompatibility of a Novel Bacterial Barrier Dressing, Wounds, 2011, 23(2):24-31.
Mironava et al., Gold Nanoparticles Cellular Toxicity and Recovery: Effect of Size, Concentration and Exposure Time, Nanotoxicology, 2010, 4(1):120-137.
Mitragotri et al., Accelerating the Translation of Nanomaterials in Biomedicine, ACS Nano, 2015, 9(7):6644-6654.
Monk et al., Potent Bactericidal Efficacy of Copper Oxide Impregnated Non-Porous Solid Surfaces, BMC Microbiology, 2014, 14(1):57, pp. 1-14.
Mora-Pale et al., Room Temperature Ionic Liquids as Emerging Solvents for the Pretreatment of Lignocellulosic Biomass, Biotechnology and Bioengineering, 2011, 108(6):1229-1245.
Mori et al., Exploring the Confirmational Space of Amorphous Cellulose Using NMR Chemical Shifts, Carbohydrate Polymers, 2012, 90(3):1197-1203.
Morris et al., The Adsorption of Microcystin-LR by Natural Clay Particles, Toxicon, 2000, 38(2):303-308.
Mundargi et al., Lycopodium Spores: A Naturally Manufactured, Superrobust Biomaterial for Drug Delivery, Advanced Functional Materials, 2016, 26(4):487-497.

(56) References Cited

OTHER PUBLICATIONS

Murugesan et al., Ionic Liquids in Carbohydrate Chemistry—Current Trends and Future Directions, Current Organic Synthesis, 2005, 2(4):437-451.

Mututuvari et al., Supramolecular Biopolymeric Composite Materials: Green Synthesis, Characterization, and Applications, Dissertation, Marquette University, 2014, 315 pages.

Narasimha et al., Antiviral Properties of Silver Nanoparticles Synthesized by Aspergillus SPS, Der Pharmacia Lettre, 2012, 4(2):649-651.

Navea et al., Application of the Local Regression Method Interval Partial Least-Squares to the Elucidation of Protein Secondary Structure, Analytical Biochemistry, 2005, 336(2):231-242.

Neidrauer et al., Near Infrared Wound Monitor Helps Clinical Assessment of Diabetic Foot Ulcers, Journal of Diabetes Science and Technology, 2010, 4(4):792-798.

Niekraszewicz, Chitosan Medical Dressings, Fibres & Textiles in Eastern Europe, 2005, 13(6):54, pp. 16-18.

Noh et al., Antibacterial Activity and Increased Freeze-Drying Stability of Sialyllactose-Reduced Silver Nanoparticles using Sucrose and Trehalose, Journal of Nanoscience and Nanotechnology, 2012, 12:1-12.

Oda et al., Reconstituted High Density Lipoprotein Enriched with the Polyene Antibiotic, Amphotericin B, Journal of Lipid Research, 2006, 47(2):260-267.

Odewunmi et al., L-Citrulline: An Active Corrosion Inhibitor Component of Watermelon Rind Extract for Mild Steel in HCl Medium, Journal of the Taiwan Institute of Chemical Engineers, 2015, 51:177-185.

Odewunmi et al., Utilization of Watermelon Rind Extract as a Green Corrosion Inhibitor for Mild steel in Acidic Media, Journal of Industrial and Engineering Chemistry, 2015, 21:239-247.

Oldfield, Chemical Shifts and Three-Dimensional Protein Structures, Journal of Biomolecular NMR, 1995, 5:217-225.

Oliver et al., Homogeneous Nucleation of n-Alkanes Measured by Differential Scanning Calorimetry, Journal of Crystal Growth, 1975, 30(3):343-351.

Othman et al., Watermelon Rind: A Potential Adsorbent for Zinc Removal, Applied Mechanics and Materials, 2014, 680:146-149.

Pan et al., Removal of Harmful Cyanobacterial Blooms in Taihu Lake Using Local Soils, III, Factors Affecting the Removal Efficiency and an In Situ Field Experiment Using Chitosan-Modified Local Soils, Environmental Pollution, 2006, 141(2):206-212.

Pan et al., Size-Dependent Cytotoxicity of Gold Nanoparticles, Small, 2007, 3(11):1941-1949.

Papazoglou et al., Noninvasive Assessment of Diabetic Foot Ulcers with Diffuse Photon Density Wave Methodology: Pilot Human Study, Journal of Biomedical Optics, 2009, 14(6):064032, pp. 1-10.

Papp et al., Inhibition of Influenza Virus Infection by Multivalent Sialic-Acid-Functionalized Gold Nanoparticles, Small, 2010, 6(24):2900-2906.

Park et al., Cellulose Composites Prepared Using Ionic Liquids (ILs)—Blood Compatibility to Batteries, Journal of American Chemical Society, 2009, Chapter 7, 1017:133-152.

Paul et al., Delivery of Antiviral Small Interfering RNA with Gold Nanoparticles Inhibits Dengue Virus Infection in Vitro, The Journal of General Virology, 2014, 95(8):1712-1722.

Pearson et al., On the Chemistry, Toxicology, and Genetics of the Cyanobacterial Toxins, Microcystin, Nodularin, Saxitoxin, and Cylindrospermopsin, Marine Drugs, 2010, 8(5):1650-1680.

Pelaz et al., The State of Nanoparticle-Based Nanoscience and Biotechnology: Progress, Promises, and Challenges, ACS Nano, 2012, 6(10):8468-8483.

Pernodet et al., Adverse Effects of Citrate/Gold Nanoparticles on Human Dermal Fibroblasts, Small, 2006, 2 (6):766-773.

Persson et al., Correlation of in Vitro Dissolution Rate and Apparent Solubility in Buffered Media Using a Miniaturized Rotating Disk Equipment: Part 1, Comparison with a Traditional USP Rotating Disk Apparatus, Drug Discoveries & Therapeutics, 2009, 3(3):104-113.

Phaechamud et al., Antibacterial Activity and Drug Release of Chitosan Sponge Containing Doxycycline Hyclate, AAPS PharmSciTech, 2008, 9(3):829-835.

Pinkert et al., Ionic Liquids and their Interaction with Cellulose, Chemical Reviews, 2009, 109(12):6712-6728.

Poduri et al., Citrullus Lanatus 'Sentinel' (Watermelon) Extract Reduces Atherosclerosis in LDL Receptor-Deficient Mice, The Journal of Nutritional Biochemistry, 2013, 24(5):882-886.

Pope et al., Absorption Spectrum (380-700 nm) of Pure Water, II, Integrating Cavity Measurements, Applied Optics, 1997, 36(33):8710-8723.

Prahl, Optical Absorption of Hemoglobin, Retrieved from https://omlc.org/spectra/hemoglobin/index.html, 1998, 4 pages.

Prahl, Tabulated Molar Extinction Coefficient for Hemoglobin in Water, Retrieved from https://omlc.org/spectra/hemoglobin/summary.html, 1998, 7 pages.

Pusateri et al., Effect of a Chitosan-Based Hemostatic Dressing on Blood Loss and Survival in a Model of Severe Venous Hemorrhage and Hepatic Injury in Swine, Journal of Trauma and Acute Care Surgery, 2003, 54(1):177-182.

Pyo et al., Adsorption of Microcystin LR by Activated Carbon Fibers, Bulletin of the Korean Chemical Society, 2005, 26(12):2089-2092.

Ribeiro et al., Burn Wounds Infected by Contaminated Water: Case Reports, Review of the Literature and Recommendations for Treatments, Burns, 2010, 36(1):9-22.

Rimando et al., Determination of Citrulline in Watermelon Rind, Journal of Chromatography A, 2005, 1078(1-2):196-200.

Ritger et al., A Simple Equation for Description of Solute Release I: Fickian and Non-Fickian Release from Non-Swellable Devices in the Form of Slabs, Spheres, Cylinders, or Discs, Journal of Controlled Release, 1987, 5(1):23-36.

Ropel et al., Octanol-Water Partition Coefficients of Imidazolium-Based Ionic Liquids, Green Chemistry, 2005, 7(2):83-90.

Rouse et al., A Review of Keratin-Based Biomaterials for Biomedical Applications, Materials, 2010, 3(2):999-1014.

Rowan et al., Burn Wound Healing and Treatment: Review and Advancements, Critical Care, 2015, 19:1-12.

Samano-Valencia et al., Characterization and Biocompatibility of Chitosan Gels with Silver and Gold Nanoparticles, Journal of Nanomaterials, 2014, 2014:543419, pp. 1-11.

Sametband et al., Effective Multi-Strain Inhibition of Influenza Virus by Anionic Gold Nanoparticles, MedChemComm, 2011, 2(5):421-423.

Sari et al., Preparation, Characterization and Thermal Properties of PMMA/N-Heptadecane Microcapsules as Novel Solid-Liquid MicroPCM for Thermal Energy Storage, Applied Energy, 2010, 87(5):1529-1534.

Sen et al., Human Skin Wounds: A Major and Snowballing Threat to Public Health and the Economy, Wound Repair and Regeneration, 2009, 17(6):763-771.

Sharma et al., Fabrication of Antibacterial Silver Nanoparticle-Sodium Alginate-Chitosan Composite Films, RSC Advances, 2012, 2(13):5837-5843.

Zegura et al., Genotoxicity and Potential Carcinogenicity of Cyanobacterial Toxins—A Review, Mutation Research/Reviews in Mutation Research, 2011, 727(1-2):16-41.

Zhang et al., Crystallization and Prevention of Supercooling of Microencapsulated N-Alkanes, Journal of Colloid and Interface Science, 2005, 281(2):299-306.

Zhang et al., Fabrication and Performances of Microencapsulated Phase Change Materials Based on N-Octadecane Core and Resorcinol-Modified Melamine-Formaldehyde Shell, Colloids and Surfaces A: Physicochemical and Engineering Aspects, 2009, 332(2-3):129-138.

Zhang et al., Synthesis and Properties of Microencapsulated N-Octadecane with Polyurea Shells Containing Different Soft Segments for Heat Energy Storage and Thermal Regulation, Solar Energy Materials and Solar Cells, 2009, 93(8):1366-1376.

Zhang et al., Design and Synthesis of Multifunctional Microencapsulated Phase Change Materials with Silver/Silica Double-Layered Shell for Thermal Energy Storage, Electrical Conduction and Antimicrobial Effectiveness, Energy, 2016, 111:498-512.

(56) References Cited

OTHER PUBLICATIONS

Zhao et al., Sustainable and Practical Utilization of Feather Keratin by an Innovative Physicochemical Pretreatment: High Density Steam Flash-Explosion, Green Chemistry, 2012, 14(12):3352-3360.
Zheng et al., Polysaccharide-Based Nanocomposites and their Applications, Carbohydrate Research, 2015, 405:23-32.
Zou et al., Removal of Cyanobacterial Blooms in Taihu Lake Using Local Soils, II, Effective Removal of Microcystis Aeruginosa Using Local Soils and Sediments Modified by Chitosan, Environmental Pollution, 2006, 141(2):201-205.
European Patent Office, Partial Supplementary European Search Report, Application No. 14797027.1, Dec. 22, 2016, 6 pages.
European Patent Office, Extended European Search Report, Application No. 14797027.1, Apr. 11, 2017, 4 pages.
European Patent Office, Extended European Search Report, Application No. 17764084.4, Oct. 31, 2019, 4 pages.
PCT International Search Report and Written Opinion, PCT/US2014/038381, Oct. 16, 2014, 8 pages.
PCT International Search Report and Written Opinion, PCT/US2017/021552, Jun. 8, 2017, 11 pages.
PCT International Search Report and Written Opinion, PCT/US2017/057134, Feb. 7, 2018, 8 pages.
PCT International Search Report and Written Opinion, PCT/US2020/038184, Sep. 24, 2020, 12 pages.
Eser et al., Antimicrobial Activity of Copper Alloys Against Invasive Multidrug-Resistant Nosocomial Pathogens, Current Microbiology, 2015, 71:291-295.
Deng et al., Superparamagnetic High-Magnetization Microspheres with an Fe3O4@SiO2 Core and Perpendicularly Aligned Mesoporous SiO2 Shell for Removal of Microcystins, Journal of the American Chemical Society, 2008, 130(1):28-29.
Docherty et al., Toxicity and Antimicrobial Activity of Imidazolium and Pyridinium Ionic Liquids, Green Chemistry, 2005, 7(4):185-189.
Feng et al., Near-Infrared Hyperspectral Imaging and Partial Least Square Regression for Rapid and Reagentless Determination of Enterobacteriaceae on Chicken Fillet, Food Chemistry, 2013, 138(2-3):1829-1836.
Khan et al., Modification and Characterization of Chitosan Films Using 3-Trimethoxysilylpropyl Methacrylate, Journal of Macromolecular Science, Part A: Pure and Applied Chemistry, 2009, 46(8):751-758.
Khosa et al., Sustainable Role of Keratin Biopolymer in Green Chemistry: A Review, Journal of Food Processing & Beverages, 2013, 1(1):8-15.
Liang et al., Preparation of Single or Double-Network Chitosan/Poly(Vinyl Alcohol) Gel Films Through Selectively Cross-Linking Method, Carbohydrate Polymers, 2009, 77(4):718-724.
Naficy et al., Modulated Release of Dexamethasone from Chitosan-Carbon Nanotube Films, Sensors and Actuators A: Physical, 2009, 155(1):120-124.
Newcombe et al., Water Treatment Options for Dissolved Cyanotoxins, Journal of Water Supply: Research and Technology—AQUA, 2004, 53(4):227-239.
Reddy et al., Bio-Thermoplastics from Grafted Chicken Feathers for Potential Biomedical Applications, Colloids and Surfaces B: Biointerfaces, 2013, 110:51-58.
Reichl, Films Based on Human Hair Keratin as Substrates for Cell Culture and Tissue Engineering, Biomaterials, 2009, 30(36):6854-6866.
Sathishkumar et al., Immobilization of Silver Nanoparticles Synthesized using Curcuma Longa Tuber Powder and Extract on Cotton Cloth for Bactericidal Activity, Biosource Technology, 2010, 101(20):7958-7965.
Siripatrawan et al., Rapid Detection of *Escherichia coli* Contamination in Packaged Fresh Spinach Using Hyperspectral Imaging, Talanta, 2011, 85(1):276-281.
Sohrabnezhad et al., Spectroscopic Study of Silver Halides in Montmorillonite and their Antibacterial Activity, Journal of Photochemistry and Photobiology B: Biology, 2016, 163:150-155.
Westad et al., Incorporating Chemical Band-Assignment in Near Infrared Spectroscopy Regression Models, Journal of Near Infrared Spectroscopy, 2008, 16(3):265-273.
Zhang et al., CuO Nanostructures: Synthesis, Characterization, Growth Mechanisms, Fundamental Properties, and Applications, Progress in Materials Science, 2014, 60:208-337.
Zheng et al., Removal of Chlorophenols from Groundwater by Chitosan Sorption, Water Research, 2004, 38(9):2315-2322.

\* cited by examiner

COMPOSITE MATERIALS CONTAINING STRUCTURAL POLYMERS AND PHOTOREACTIVE NITRIC OXIDE RELEASING AGENTS AND USES THEREOF FOR WOUND DRESSINGS

CROSS-REFERENCE TO RELATED PATENT APPLICATIONS

The present application is a continuation in part of International Application No. PCT/US2017/057134, filed on Oct. 18, 2017, which application claims the benefit of priority under 35 U.S.C. § 119(e) to U.S. Provisional Application No. 62/409,617, filed on Oct. 18, 2016, the contents of which applications are incorporated herein by reference in their entireties.

BACKGROUND

The field of the invention relates to wound dressings comprising composite materials containing structural polysaccharides, structural proteins, and nitric oxide (NO) releasing agents, and ionic liquid compositions for preparing the composite materials. In particular, the field of the invention relates to composite materials containing structural polysaccharides, such as cellulose, chitin, or chitosan, structural proteins, such as keratin, and photoreactive nitric oxide (NO) releasing agents, which composite materials are formed from ionic liquid compositions.

SUMMARY

Disclosed herein are compositions and composite materials comprising one or more structural polymers and one or more nitric oxide releasing agents. Suitable structural polymers may include structural polysaccharides, structural proteins, or mixtures thereof. Preferably, the nitric oxide releasing agents of the composite materials are photo-reactive nitric oxide releasing compounds or complexes, for example, where the nitric oxide releasing compounds or complexes may be loaded with nitric oxide and treated with light to induce release of the loaded nitric oxide.

The composite materials may be prepared from ionic liquid compositions comprising the one or more structural polymers and the one or more nitric oxide releasing agents dissolved in the one or more ionic liquids forming the liquid ionic composition. The composite materials may be prepared from the ionic liquid compositions, for example, by removing the ionic liquid from the ionic liquid composition and retaining the one or more structural polymers, and the one or more nitric oxide releasing agents. The nitric oxide releasing agents may be loaded with nitric oxide by exposing the composite material comprising the nitric oxide releasing compounds to a nitric oxide stream.

The disclosed composite materials typically comprise one or more structural polymers. Suitable structural polymers may include structural polysaccharides, structural proteins, or mixtures thereof Suitable polysaccharides may include, but are not limited to polymers such as polysaccharides comprising monosaccharides linked via beta-1,4 linkages. For example, suitable structural polysaccharides may include polymers of 6-carbon monosaccharides linked via beta-1,4 linkages. Suitable structural polysaccharides for the disclosed compositions and composites may include, but are not limited to cellulose, chitin, and modified forms of chitin such as chitosan.

The disclosed compositions and composites preferably comprise one or more structural proteins. Suitable structural proteins may include, but are not limited to, keratin. Natural components that comprise keratin may be used to prepare the disclosed composite materials include wool, human hair, and/or chicken feathers.

The disclosed compositions and composites preferably comprise one or more nitric oxide releasing agents, which may include nitric oxide releasing compounds or complexes. Suitable nitric oxide releasing compounds may include photo-reactive or photolyzable nitric oxide compounds or complexes.

The disclosed compositions and composites optionally may include additional active agents. Suitable active agents may include anti-microbial agents, such as ciprofloxacin (e.g., Cipro™), or other anti-bacterial agents or anti-fungal agents.

The disclosed compositions and composites optionally may include one or more metal or metal oxide nanoparticles. Preferably, the one or more metal and/or metal oxide nanoparticles are added to the one or more ionic liquid compositions, for example, as metal salts which subsequently are reduced in situ.

The disclosed composite materials may be formed from ionic liquid compositions, for example, ionic liquid compositions comprising the one or more structural polymers dissolved in one or more ionic liquids to form an ionic liquid composition, where preferably, the one or more nitric acid releasing compounds are added to the ionic liquid composition. Suitable ionic liquids for forming the ionic liquid compositions may include but are not limited to alkylated imidazolium salts. In some embodiments, the alkylated imidazolium salt is selected from a group consisting of 1-butyl-3-methylimidazolium salt, 1-ethyl-3-methylimidazolium salt, and 1-allyl-3-methylimidazolium salt. Suitable salts may include, but are not limited to chloride salts.

In the disclosed ionic liquid compositions, a structural polysaccharide may be dissolved in an ionic liquid. In some embodiments, the ionic liquid may comprise at least about 2%, 4%, 6%, 8%, 10%, 15%, 20% w/w, dissolved structural polysaccharide.

In the disclosed ionic liquid compositions, a structural protein may be dissolved in the ionic liquid. In some embodiments, the ionic liquid may comprise at least about 2%, 4%, 6%, 8%, 10%, 15%, 20% w/w, dissolved structural protein.

The disclosed ionic liquid compositions may be utilized in methods for preparing the disclosed composite materials that comprise a structural polymer and one or more nitric oxide releasing agents. For example, in the disclosed methods, a composite material comprising a structural polysaccharide and/or a structural protein, and one or more nitric oxide releasing agents may be prepared by: (1) obtaining or preparing an ionic liquid composition as disclosed herein comprising a structural polysaccharide and/or a structural protein, where the structural polysaccharide and/or the structural protein are dissolved in an ionic liquid to form an ionic liquid composition; (2) adding one or more nitric oxide releasing agents to the ionic liquid composition; (3) removing the ionic liquid from the ionic liquid composition; and (4) retaining the structural polysaccharide and/or the structural protein, and the nitric oxide releasing agents as a composite material. The ionic liquid may be removed from the ionic liquid compositions by steps that include, but are not limited to washing (e.g., with an aqueous solution). The water remaining in the composite materials after washing may be removed from the composite materials by steps that include, but are not limited to drying (e.g., in air) and lyophilizing (i.e., drying under a vacuum). The composite material may be formed into any desirable shape, for example, a film and/or fabric material. The composite material may be utilized to prepare a dressing for a wound.

The composite material may be utilized to kill or eliminate microbes, including but not limited to bacteria and fungi. For example, the composite material may be contacted with bacteria and fungi including but not limited to *Staphylococcus aureus* (including methicillin-resistant strains (MRSA)), and *Enterococcus faecalis* (including vancomycin-resistant strains), *Pseudomonas aeruginosa, Escherichia coli, Candida albicans* in order to kill or eliminate the microorganisms.

In other embodiments, the composite materials may be utilized to carry and release a compound. For example, the composite materials may be utilized to carry and release a compound gradually over an extended period of time (e.g., nitric oxide and/or a drug such as ciprofloxacin, or a compound such as 1-methylocyclopropene in order to kill bacteria in ulcerous infected wounds and/or to delay ripening of fruit or freshness of flowers). As such, the composite material may be utilized in wound dressing material or bandages (e.g., for chronic, ulcerous infected wounds).

DETAILED DESCRIPTION

Figure 1:
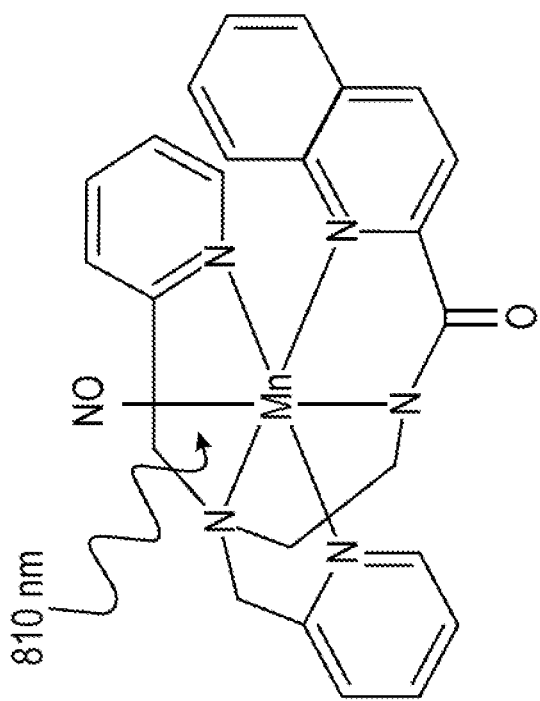
FIG. 1. Near-infrared light (810 nm) applied to NO-loaded complex (2) induces release of NO for $H_2O$.
Figure 1:
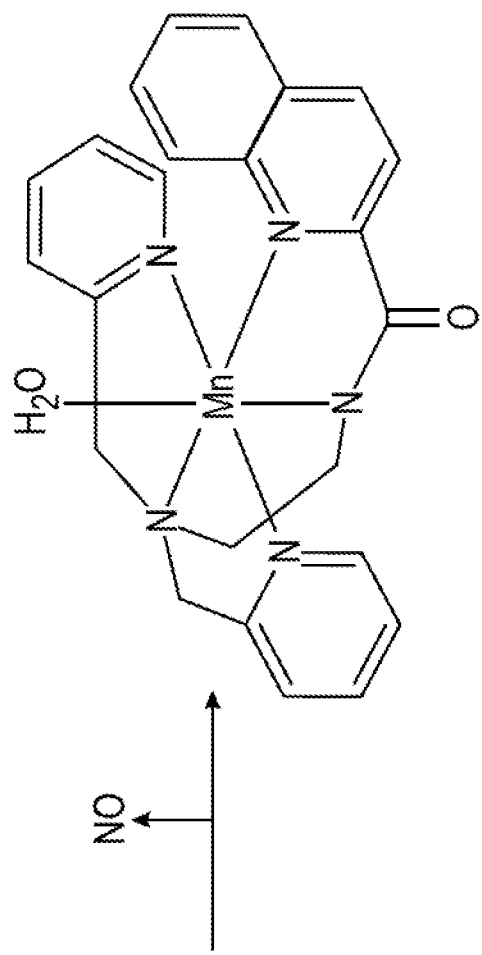

The disclosed subject matter further may be described utilizing terms as defined below.

Unless otherwise specified or indicated by context, the terms "a", "an", and "the" mean "one or more." For example, "a compound" should be interpreted to mean "one or more compounds."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of" while encompassed by the term "comprising," should be interpreted as a "closed" transitional term that limits claims only to the recited elements succeeding this transitional term. The term "consisting essentially of" while encompassed by the term "comprising," should be interpreted as a "partially closed" transitional term which permits additional elements succeeding this transitional term, but only if those additional elements do not materially affect the basic and novel characteristics of the claim.

Disclosed are composite materials and ionic liquid compositions for preparing the composite materials. The composite materials typically include one or more structural polymers (which may include structural polysaccharides and/or structural proteins) and one ore more nitric oxide releasing agents.

As used herein, "structural polysaccharides" refer to water insoluble polysaccharides that may form the biological structure of an organism. Typically, structurally polysaccharides are polymers of 6-carbon sugars such as glucose or modified forms of glucose (e.g., N-acetylglucosamine and glucosamine), which are linked via beta-1,4 linkages. Structural polysaccharides may include, but are not limited to cellulose, chitin, and chitosan, which may be formed from chitin by deacetylating one or more N-acetylglucosamine monomer units of chitin via treatment with an alkali solution (e.g., NaOH). Chitosan-based polysaccharide composite materials and the preparation thereof are disclosed in Tran et al., J. Biomed. Mater. Res. Part A 2013:101A:2248-2257 (hereinafter "Tran et al. 2013), which is incorporated herein by reference.

As used herein, a "structural protein" is a protein that is used to build structural components of a body. Suitable structural proteins for the disclosed composite materials may include but are not limited to keratin. Keratin for use in the disclosed methods for preparing the disclosed composite materials may be derived from a number of sources, including but not limited to wool, human hair, and chicken feathers.

The disclosed composite materials may be prepared from ionic liquid compositions that comprise one or more structural polysaccharides and/or one ore more structural proteins dissolved in one or more ionic liquids. As used herein, an "ionic liquid" refers to a salt in the liquid state, typically salts whose melting point is less than about 100° C. Ionic liquids may include, but are not limited to salts based on an alkylated imidazolium cation, for example,

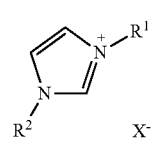

where $R^1$ and $R^2$ are C1-C6 alkyl (straight or branched), and $X^-$ is any cation (e.g., a halide such as chloride, a phosphate, a cyanamide, or the like).

The disclosed compositions preferably comprise one or more nitric oxide releasing agents, which may include nitric oxide releasing compounds or complexes. Suitable nitric oxide releasing compounds may include photo-reactive or photolyzable nitric oxide donor compounds or complexes which may be loaded with nitric oxide and subjected to light in order to release the loaded nitric oxide.

In some embodiments, the nitric oxide releasing compound or complex of the disclosed composites is a photo-reactive metal complex that binds and releases nitric oxide. Suitable nitric oxide releasing compounds may include photo-reactive transition metal complexes that bind and release nitric oxide. Photo-reactive compounds have been described in the art. (See e.g. Iwamoto et al., "Uncaging a catalytic hydrogen peroxide generator through the photo-induced release of nitric oxide from a {MnNO}6 complex," Chem. Commun., 2015, 51, 9539-9542; Hitomi et al., "Electronic tuning of nitric oxide release from manganese nitrosyl complexes by visible light irradiation: enhancement of nitric oxide release efficiency by the nitro-substituted quinolone ligand," Dalton Trans., 2014, 43, 2161-2167; and Eroy-Reveles et al., "Near-Infrared Light Activated Release of Nitric Oxide from Designed Photoactive Manganese Nitrosyls: Strategy, Design, and Potential as NO Donors," J. Am. Chem. Soc. 2008, 130, 4447-4458; U.S. Pat. Nos. 8,609,843; 7,122,529; and 5,374,710; the contents of which are incorporated herein by reference in their entireties).

Suitable photo-reactive transition metal complexes may include complexes of formula (1) or (2) which may be irradiated (e.g., with near infrared light having a wavelength of 600 nm to 2500) in order to induce the complexes to release nitric oxide.

(1)

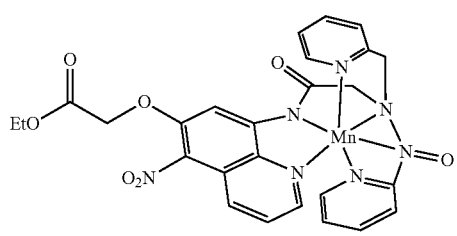

(2)

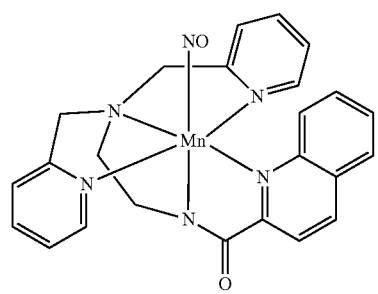

Complex (1) forms from Manganese (Mn) coordinating with the following compound:

(1a)

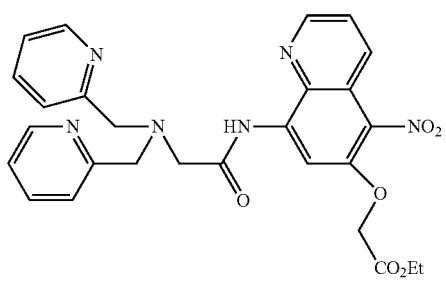

Complex (2) forms from Mn coordinating with the following compound:

(2a)

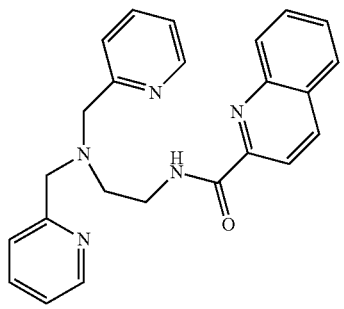

Complex (1) and (2) can be induced to release NO by irradiating the complex with near-infrared light, for example, as illustrated in FIG. 1.

Composite material comprising the photo-reactive nitric oxide releasing agents may be loaded within nitric oxide and utilized as a wound dressing. Subsequently, the dressing may be irradiated in order to induce release of nitric oxide from the composite material and promote wound healing and inhibit microbial growth.

The disclosed compositions and composites may include additional active agents. Suitable active agents may include anti-microbial agents (e.g., anti-bacterial agents, and anti-fungal agents). Suitable anti-microbial agents may include, but are not limited to ciprofloxacin, amoxicillin, doxycycline, azithromycin, erythromycin, roxithromycin, flucloxacillin, metronidazole, co-trimoxazole, cephalexin, and the like. As disclosed herein the release of anti-microbial agents incorporated into the disclosed composite materials may be controlled, for example, based on the concentration of structural protein in the composite material such as keratin.

The disclosed compositions and composites may include metal or metal oxide nanoparticles. As used herein, the term "nanoparticle" generally means particles having an average effective diameter of less than about 1 micron, for example, particles having an average effective diameter of about 100 nm-800 nm. Suitable metals for the nanoparticles may include gold, silver, or copper oxide nanoparticles. Optionally, metal oxide nanoparticles (i.e., where the metal has a positive valence) may be incorporated into the disclosed composite material and reduced in situ to produce composite material comprising metal nanoparticles (i.e., where the metal has zero valence). Methods for preparing the disclosed composites comprising metal particles are disclosed in Tran et al., ACS Appl. Mater. Interfaces, 2016, 8 (50), pp 34791-34801; and Tran et al., J. Colloid and Interface Science, 2017 Sep. 6; 510:237-245; the contents of which are incorporated herein by reference in their entireties.

ILLUSTRATIVE EMBODIMENTS

The following embodiments are illustrative and are not intended to limit the scope of the claimed subject matter.

Embodiment 1

An ionic liquid composition comprising: (a) a structural polysaccharide and/or a structural protein dissolved in an ionic liquid; and (b) a nitric oxide binding/releasing agent dissolved in the ionic liquid.

Embodiment 2

The composition of embodiment 1, wherein the structural polysaccharide is a polymer comprising 6-carbon monosaccharides linked via beta-1,4 linkages.

Embodiment 3

The composition of any of the foregoing embodiments, wherein the structural polysaccharide comprises cellulose.

Embodiment 4

The composition of any of the foregoing embodiments, wherein the structural polysaccharide comprises chitin.

Embodiment 5

The composition of any of the foregoing embodiments, wherein the structural polysaccharide comprises chitosan.

Embodiment 6

The composition of any of the foregoing embodiments, wherein the structural protein comprises keratin.

Embodiment 7

The composition of embodiment 1, wherein the nitric oxide releasing agent is a transition metal complex.

Embodiment 8

The composition of any of the foregoing embodiments, further comprising an anti-biotic agent such as ciprofloxacin.

Embodiment 9

The composition of any of the foregoing embodiments, further comprising metal nanoparticles and/or metal oxide nanoparticles.

Embodiment 10

The composition of embodiment 9, wherein the metal nanoparticles comprise gold, silver, or copper nanoparticles and/or wherein the metal oxide nanoparticles comprise gold, silver, or copper oxide nanoparticles.

Embodiment 11

The composition of any of the foregoing embodiments, wherein the ionic liquid is an alkylated imidazolium salt.

Embodiment 12

The composition of embodiment 11, wherein the alkylated imidazolium salt is selected from a group consisting of 1-butyl-3-methylimidazolium salt, 1-ethyl-3-methylimidazolium salt, and 1-allyl-3-methylimidazolium salt.

Embodiment 13

The composition of any of the foregoing embodiments, wherein the ionic liquid is 1-butyl-3-methylimidazolium chloride.

Embodiment 14

The composition of any of the foregoing embodiments, wherein the ionic liquid composition comprises at least 4% w/w of the dissolved structural polysaccharide and/or structural protein.

Embodiment 15

The composition of any of the foregoing embodiments, wherein the ionic liquid composition comprises at least 10% w/w of the dissolved structural polysaccharide and/or structural protein.

Embodiment 16

A method for preparing a composite material comprising a structural polysaccharide and/or a structural polypeptide, and a nitric oxide binding/releasing agent, the method comprising: (a) dissolving the structural polysaccharide and/or the structural polypeptide and the nitric oxide releasing/binding agent dissolved in an ionic liquid, and (b) removing the ionic liquid to obtain the composite material.

Embodiment 17

The method of embodiment 16, further comprising contacting the composite material with nitric oxide after removing the ionic liquid to load the nitric oxide releasing agent with nitric oxide.

Embodiment 18

The method of embodiments 16 or 17, wherein the ionic liquid is removed by steps that include washing the ionic liquid composition with an aqueous solution to obtain the composite material and drying the composite material thus obtained.

Embodiment 19

The method of any of embodiments 16-18, wherein the composite material further comprises metal or metal oxide nanoparticles and the method further comprises dissolving the metal or metal oxide nanoparticles in the ionic liquid.

Embodiment 20

A composite material prepared by the method of any of embodiments 16-19.

Embodiment 21

A method for delivering nitric oxide to a wound, the method comprise: (a) contacting the composite material of embodiment 20 with a wound, wherein the composite material comprises the nitric oxide releasing agent loaded with nitric oxide; and (b) irradiating the composite material with near-infrared light to release nitric oxide releasing agent.

Embodiment 22

The method of embodiment 21, wherein the near-infrared light has a wavelength between about 600-900 nm (preferably about 650 nm and/or about 810 nm).

Embodiment 23

A dressing for a wound comprising the composite material of embodiment 20.

Examples

The following examples are illustrative and are not intended to limit the claimed subject matter.

Figure 2:
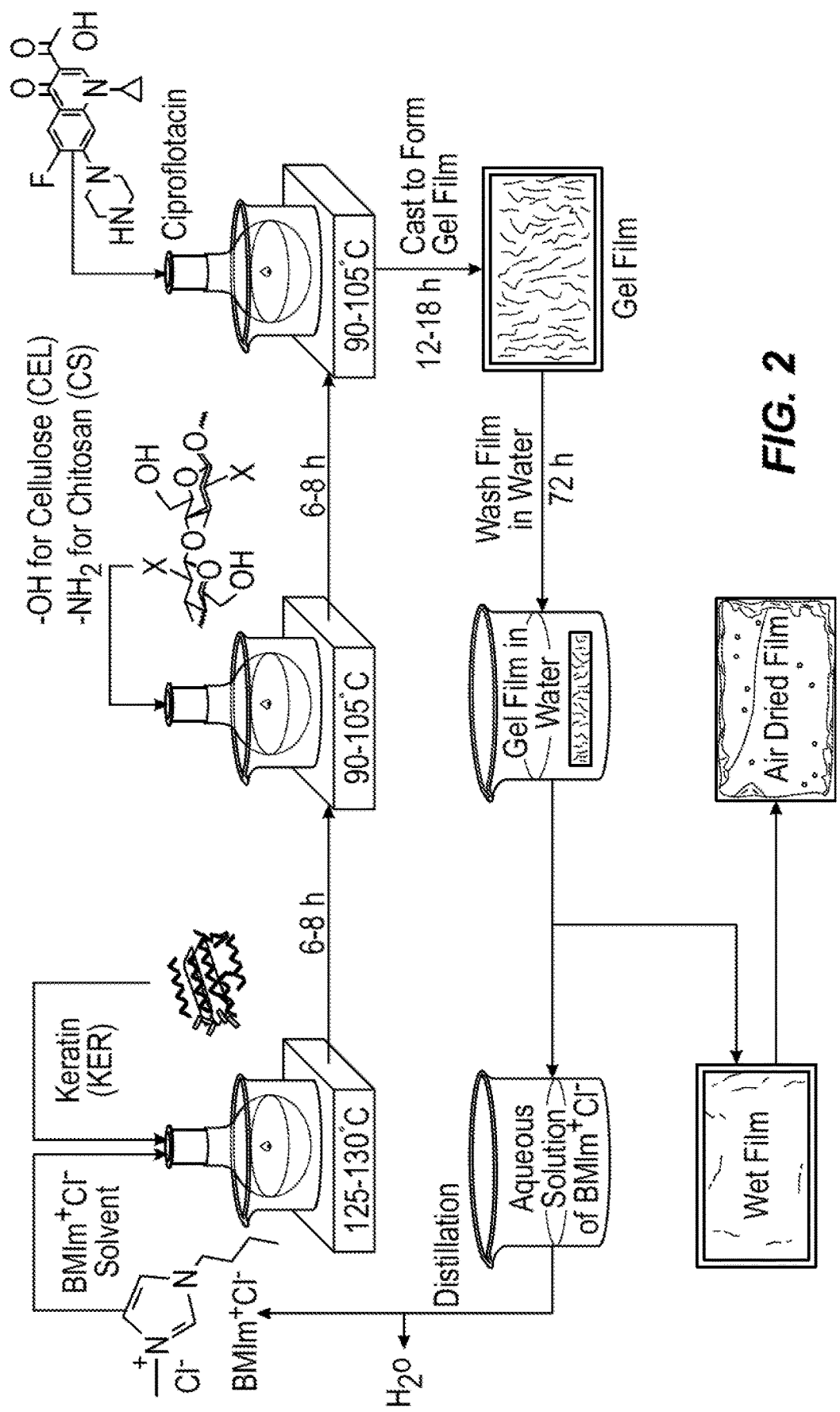
FIG. 2. Scheme summarizing the method used to synthesize the composites containing cellulose, chitosan and keratin from three different sources (wool, hair and chicken feathers).

Example 1—Synthesis of Composite Materials and Composite Materials Comprising Metal Nanoparticles We developed a novel, green, pollution-free and totally recyclable method to synthesize biocompatible composites from biorenewable natural polymers such as cellulose (CEL), chitosan (CS) and keratin (KER from different sources (wool, human hair, chicken)) by using ionic liquid (IL), an organic salt that is liquid at room temperature as the sole solvent. (See FIG. 2; see also Tran et al., Langmuir 2015, 31, 1516-1526; the content of which is incorporated herein by reference in its entirety). IL has unique chemical and physical properties, including being air and moisture stable, a high solubility power, and virtually no vapor pressure, and is a "Green" recyclable alternative to the traditionally volatile organic solvents. Using the developed method, we prepared a composite comprising CEL, CS and KER, otherwise referred to as a [CEL+CS+KER] composite. We found that the amounts of the polymer components of the composites can be varied to affect the properties of the composite, including properties related to drug release.

Figure 3:
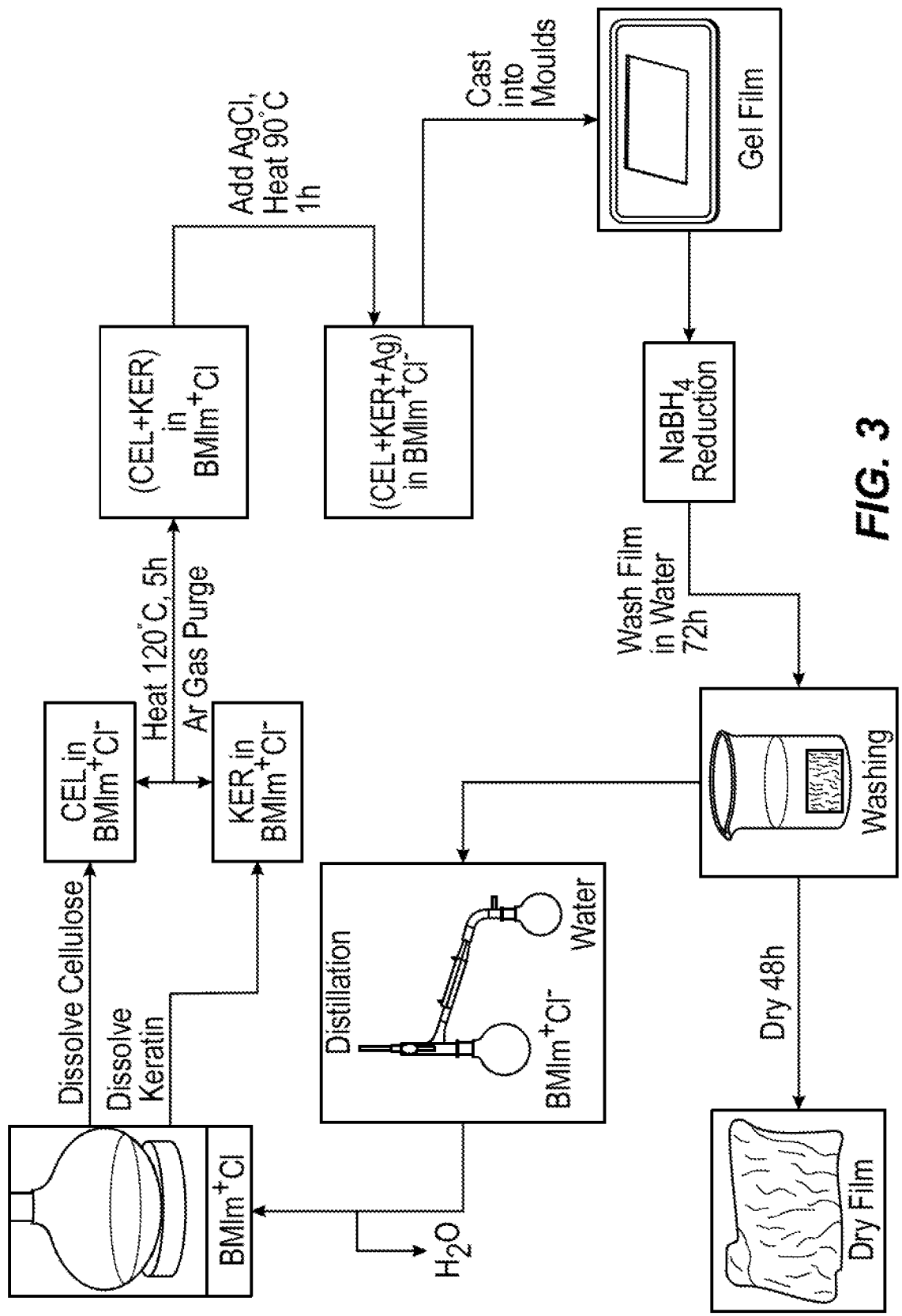
FIG. 3. Scheme summarizing the method used to synthesize (CEL+CS+KER) composites containing gold, silver or copper nanoparticles. AgCl is illustrated as an exemplary salt that is incorporated into the composite material and subsequently reduced to provide composite material comprising silver (0) particles.

We also introduced gold, silver and copper oxide nanoparticles (AgNPs, AuNPs and CuONPs) to the [CEL+CS+KER] composite to further improve performance of the composite materials, i.e., to render the composite materials with improved properties to remove pollutants, to deliver drugs, and to kill bacteria and viruses. To accomplish this goal, we developed a green synthetic method in which metal salts (i.e., AgCl, $HAuCl_4$ and Cu(OAc)) were introduced into the composites during the dissolution of the biopolymers by IL. (See FIG. 3; see also Tran et al., ACS Appl. Mater. Interfaces, 2016, 8 (50), pp 34791-34801; and Tran et al., J. Colloid and Interface Science, 2017 Sep. 6; 510:237-245; the contents of which are incorporated herein by reference in their entireties). Subsequently the metal salts were reduced directly in the composites, not by using traditional reducing reagents such as $NaBH_4$ or citrate but rather by contacting the metal salts with watermelon rind extract to make the entire process completely "Green." The composite materials thus prepared are biocompatible and retain the properties of their components (e.g., facilitating wound healing, adsorption of pollutants and toxins, antimicrobial and antiviral activity, and drug delivery capability).

We characterized the nanoparticles composites with various spectroscopic methods, and performed assays to demonstrate that composite materials are superior to other materials, namely, we carried out bioassays to determine activity of the composites toward different bacteria (*S. aureus*, *E coli*, methicillin resistant *S. aureus* (MRSA), and vancomycin resistant Enterococcusfaecalis (VCE)), bacteriophages (MR2, FR, Phi-XI 74) and viruses (aenovirus type 4, feline calicivirus, and echovirus 12).

The disclosed composites include several advantageous characteristics. First, the composite materials are Green, biocompatible, and may be used for pollutant adsorption, drug delivery, an antimicrobial and antiviral properties. The composite materials are synthesized from sustainable biorenewable biopolymers including polysaccharides (cellulose and chitosan) and protein (keratin from wool, hair and chicken feather). Second, the composite material may include gold, silver and copper oxide nanoparticles (AgNPs, AuNPs and CuONPs) which are introduced to the [CEL+CS+KER] composites to improve the stability of the nanoparticles (e.g., by preventing them from aggregation and leakage during repeating use). The nanoparticles further improve performance of the composite materials, i.e., to render them more efficient for removing pollutants, for stopping bleeding and healing ulcerous wounds, for delivering drugs, and for killing bacteria and viruses. Finally, the synthetic method for preparing the disclosed composite materials is recyclable (i.e., all chemicals used are recovered for reuse with no waste) and totally green (e.g., watermelon rind is used instead of reactive and corrosive reducing reagents such as sodium borohydride).

The contributions of this invention to the field of analytical chemistry, materials science and biomedical applications are invaluable because, in contrast to other existing techniques, this green and totally recyclable method will provide an inexpensive and easy process to synthesize novel nanoparticle composites from abundant, natural biopolymers. The composite obtained will advance the field of pollutant and toxin removal, bactericide, virucide, and drug delivery, and the development of novel and/or improved methods for (1) novel biocompatible antimicrobial agents to combat antibiotic resistant bacteria and fungi or "superbugs;" (2) purification elements for drinking water; and (3) and high performance bandage material to treat diabetic ulcerous wounds. Moreover, by fabricating the composite material from abundant, natural biopolymers using eco-friendly Green synthetic methods, the nanoparticle composites are sustainable, nontoxic, biocompatible, and can be used for external and internal use without prior FDA approval. Thus, they lead to safer products and a better environment.

Example 2—Synthesis of Composite Materials Comprising Complexes for Nitric Oxide Loading and Release

Introduction

Nitric oxide (NO) plays an essential role in various biological functions such as angiogenesis, apoptosis, immune response, neurotransmission, and cardiovascular homeostasis.[1] For example, NO is a key factor for wound healing. In the early wound, high NO levels are produced by inflammatory cells to fight infection. As the wound heals, endothelial cells, fibroblasts and keratinocytes produce lower sustained NO amounts to stimulate angiogenesis and new tissue formation.[1] Exogenously generated NO is known to have therapeutic potential for the treatment and healing of infected wounds.[10] As a consequence, many NO delivery systems including NO donors such as alkyl nitrites, transition-metal nitrosyl complexes, nitrosamines, N-diazoniumdiolates, and S-nitrosothiols (RSNOs) have been developed.[2] However, a variety of factors severely limit the success of these methods including NO short half-life, instability of NO donors and rapid and/or inconsistent release of NO.[2,3] This is, because, as described above, the biological effects of NO are highly dependent on concentration and dosage.

Of interest are the recent reports on a new class of the photoactive NO donors which, upon irradiating with light, can deliver spatially and temporally controlled NO to a specific target.[4-8] Photoreactive manganese complexes (1) and (2) are of particular importance as they have relatively high photorelease quantum yields (0.780 and 0.694 for (1) and (2)) and can quickly release NO when irradiated with light in the near-IR region (650 nm and 810 nm) where most materials including tissues and [CEL+CS+KER] composites do not absorb.[4-8]

As shown herein, we are able to encapsulate antibiotics such as ciprofloxacin into a cellulose, chitosan, keratin composite "[CEL+CS+KER]" for subsequently released when the [CEL+CS+KER] composite is used as a wound dressing.[9] The kinetics of the Cipro release can be controlled by judiciously adjusting the concentration of KER in the composite.[9]

While NO is a bactericide, it is typically used not to completely replace antibiotics such as Cipro but rather to complement Cipro. Specifically, we can use [CEL+CS+KER] composites to provide controlled release of an antibiotic such as Cipro and/or other antibiotic for treatment of wounds infected by bacteria and fungi. A similar composite but which contains a photoactive NO donor such as complex (1) or (2) may also kill bacteria but the types and number of bacteria it can be kill may not be the same as those killed by ciprofloxacin.

Moreover, NO is not only a bactericide but also is involved in all facets of the wound healing process including anti-inflammation, angiogenesis, and cell proliferation. As a consequence, ciprofloxacin (and/or other antibiotic) and NO can be synergistically used by encapsulating them into the same [CEL/CS+KER] composite. Any bacteria and fungi that are not initially killed by ciprofloxacin will be subsequently killed by NO upon irradiating, and the NO released will also promote anti-inflammation and tissue regenerating.

I propose to encapsulate antibiotics such as ciprofloxacin and NO photoreactive complexes such as complexes (1) or (2) in the [CEL+CS+KER] composites during the synthetic process. The resulting composites may be referred to as [CEL+CS/KER+(1)/(2)] composites. The composites, when use as a wound dressing, can deliver antibiotics to wound with controlled kinetics (by adjusting the concentration of KER in the composite). NO can be delivered by the composite dressing at will and with temporal and spatial control by irradiating the composite with near-infrared light (from a diode laser) at either 650 nm or 810 nm for complexes (1) and (2), respectively, which results in complexes (1) or (2) releasing any bound NO. Such photorelease is possible because the [CEL+CS+KER] composites are transparent in the NIR region, namely light at 650 nm and 810 nm can go through the composite and will promote photoreaction in complexes (1) or (2) for them to release NO. While complexes (1) and (2) have been previously synthesized, to date, there is no report on their use in a dressing to provide controlled release of NO by photoirradiating.

Methods

Preparation of [CEL+CS/KER+(1)/(2)] Composites

Figure 4:
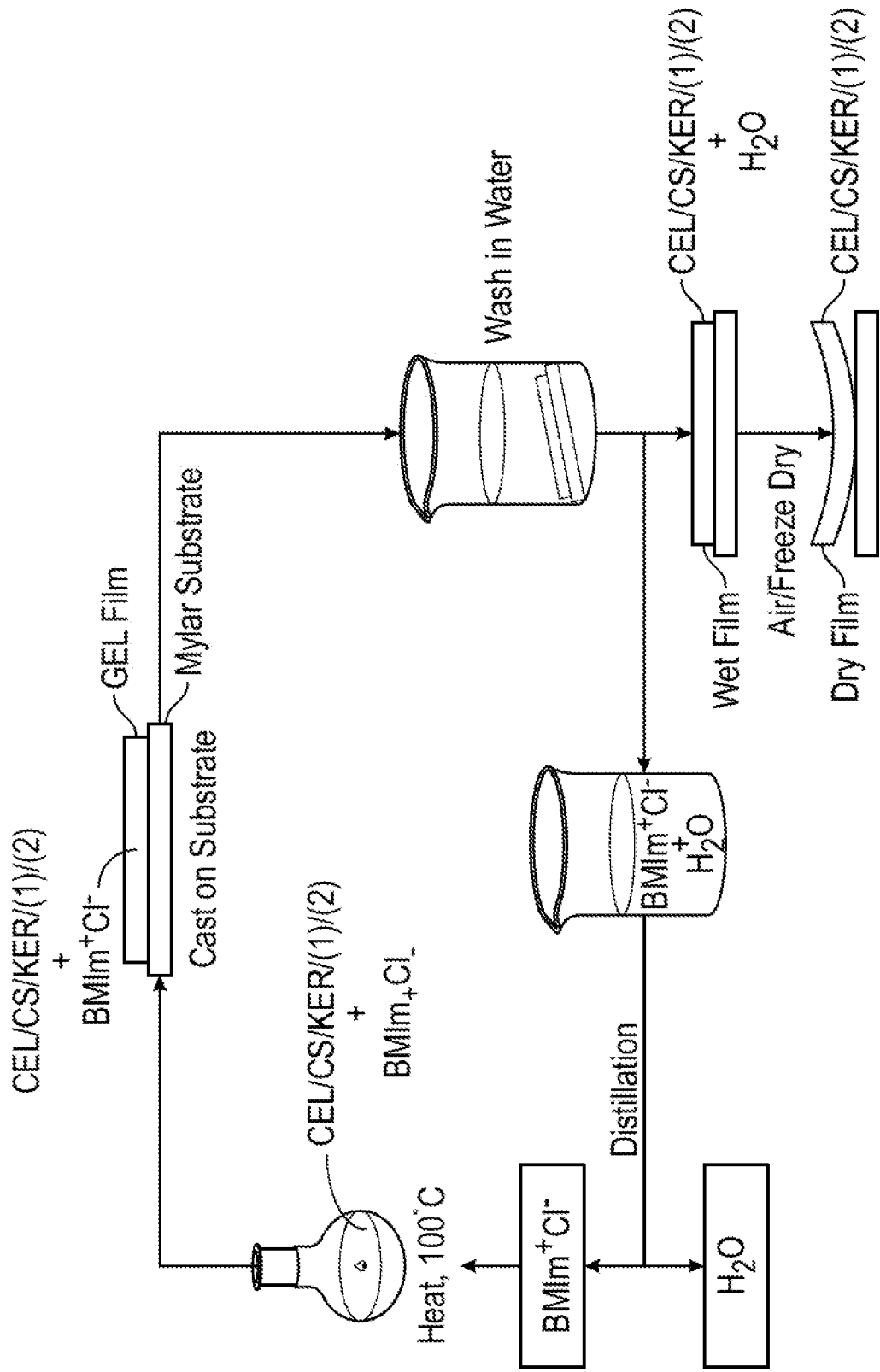
FIG. 4. Procedure used to synthesize [CEL+CS/KER] composites containing nitric oxide binding/releasing complexes (1) and (2).

NIR absorbing photorelease complexes (1) or (2) will be encapsulated into the [CEL+CS] or [CEL+KER] composite during the preparation process. As shown in FIG. 4, an ionic liquid, butylmethylimmidazolium chloride ([BMIm$^+$Cl$^-$]) will be used as a solvent to dissolve CEL, CS or KER and complexes (1) or (2). Dissolution will be performed at 100° C. and under Ar or N$_2$ atmosphere. All biopolymers will be added in portions of approximately 1 wt % of the ionic liquid. Succeeding portions will be only added after the previous addition has completely dissolved until the desired concentration has been reached. For composite films, the components will be dissolved one after the other, with KER (or CS) being dissolved first followed by CEL and complexes (1) or (2) last. Using this procedure, ([BMIm$^+$Cl$^-$] solutions of CEL, KER or CS and complexes (1) or (2) with various proportions will be prepared.

Upon complete dissolution, the homogeneous [BMIm$^+$Cl$^-$] solutions of the biopolymers and complexes (1) or (2) [BMIm$^+$Cl$^-$] will be cast on glass slides or Mylar sheets using a RDS stainless steel coating rod with appropriate size (RDS Specialties, Webster, N.Y.) to produce thin films with different compositions and concentrations of CEL, CS (or KER) with photorelease complexes (1) or (2). If necessary, thicker composite materials can be obtained by casting the solutions onto PTFE molds of the desired thickness. They will then be kept at room temperature for 24 hours to allow the solutions to undergo gelation to yield GEL Films. The [BMIm$^+$Cl$^-$] remaining in the film will then be removed by washing the films in deionized water for about 3 days to yield WET Films. During this period, the washing water will be constantly replaced with fresh deionized water to maximize the removal of the ionic liquid. The [BMIm$^+$Cl$^-$] used will be recovered from the washed aqueous solution by distillation. The regenerated composite materials were lyophilized overnight to remove water, yielding dried porous composite films (DRY films).

Procedure to Release NO from [CEL+CS/KER+(1)] Composites and [CEL+CS/KER+(2)] Composites.

NO release from the composite into water will be determined by placing a 2 cm×2 cm section of composite containing either complexes (1) or (2) into 20 mL of distilled water in a closed flash. NO will be released from the composite when it is irradiated with a NIR diode laser at 650 nm for complexes (1) or 810 nm for (2). The concentration of released NO in water will be determined by the Sievers Nitric Oxide Analyzer (NOA 280i) via NO$_2$ chemiluminescence, which is formed by reacting NO with O3 that is generated by the analyzer.[195] The NO analyzer is highly sensitive (1 pmole LOD) and has a wide dynamic range (nmolar to mmolar). The amount of NO released as a function of time will be measured and data obtained will be fitted to the Korsmeyer-Peppas power law model to determine the kinetics of release. Release rates at different concentrations of encapsulated complexes (1) or (2) and intensity of the 650 nm or 810 nm light (from either a 200 W argon arc lamp (Oriel model 66002) and an Oriel 125 mm monochromator or LED at 650 nm or 810 nm) will be measured to obtain correlations for subsequent use in controlling and varying the rate.

REFERENCES

1. L Y. Yang, P. L, Qi, Z. L. Yang and N. Huang, Nitric oxide based strategies for applications of biomedical devices, Biosurface Biotribology, 1, 177-201 (2015).
2. J. Kim, G. Saravanakumar, H. W. Choi, D. Park and W. J. Kim, A platform for nitric oxide delivery J. Mat. Chem. B, 2, 341-356 (2014). T. Welton, "Room-Temperature Ionic Liquids. Solvents for Synthesis and Catalysis", Chem. Rev., 1999, 99, 2071-2083.
3. Cohen Stuart, M. A.; Huck, W. T. S.; Genzer, J; Mueller, M.; Ober, C.; Stamm, M.; Sukhorukov, G. B.; Szleifer, I.; Tsukruk, V. V.; Urban, Marek; et al, Emerging applications of stimuli-responsive polymer materials, Nature Materials (2010), 9(2), 101-113 (2010).
4. Yuji Iwamoto, Masahito Kodera and Yutaka Hitomi, Uncaging a catalytic hydrogen peroxide generator through the photo-induced release of nitric oxide from a {MnNO}6 complex, Chem. Commun., 2015, 51, 9539-9542.
5. Yutaka Hitomi, Yuji Iwamoto and Masahito Kodera, Electronic tuning of nitric oxide release from manganese nitrosyl complexes by visible light irradiation: enhancement of nitric oxide release efficiency by the nitro-substituted quinolone ligand, Dalton Trans., 2014, 43, 2161-2167.
6. Aura A. Eroy-Reveles, Yvonne Leung, Christine M. Beavers, Marilyn M. Olmstead, and Pradip K. Mascharak, Near-Infrared Light Activated Release of Nitric Oxide from Designed Photoactive Manganese Nitrosyls: Strategy, Design, and Potential as NO Donors, J. Am. Chem. Soc. 2008, 130, 4447-4458.
7. Karl J. Koebke, Daniel J. Pauly, Leonid Lerner, Xien Liu, † and A. Andrew Pacheco, Does the Oxidation of Nitric Oxide by oxyMyoglobin Share an Intermediate with the met Myoglobin-Catalyzed Isomerization of Peroxynitrite?, Inorg. Chem, 2013, 52, 7623-7632.
8. Karl J. Koebke, Michael T. Waletzko, Andrew Pacheco, Direct monitoring of the reaction between photochemically generated nitric oxide and *Mycobacterium tuberculosis* truncated hemoglobin N will type and variant forms: an assessment of computational mechanistic predictions, Biochemistry, 2016, 55, 686-696.
9. Chieu D. Iran and Tamutsiwa Mututuvari "Cellulose, Chitosan and Keratin Composite Materials, Controlled Drug Release", Langmuir, 31, 1516-1526 (2015).
10. Simon Duri and Chieu D. Tran, "Supramolecular Composite Materials from Cellulose, Chitosan, and Cyclodextrin: Facile Preparation and Their Selective Inclusion Complex Formation with Endocrine Disruptors," Langmuir 29, 5037-5049 (2013).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

I claim:

1. A composite material comprising cellulose, keratin, and a nitric oxide binding/releasing agent, wherein the nitric oxide binding/releasing agent is a complex comprising a manganese atom (Mn) coordinated with ligands which complex binds nitric oxide and releases nitric oxide when irradiated with near-infrared light having a wavelength between 600 nm and 900 nm.

2. The composite material of claim 1, further comprising an anti-biotic agent.

3. The composite material of claim 1, further comprising metal nanoparticles and/or metal oxide nanoparticles.

4. The composite material of claim 3, wherein the metal nanoparticles comprise gold, silver, or copper nanoparticles and/or wherein the metal oxide nanoparticles comprise gold, silver, or copper oxide nanoparticles.

5. The composite material of claim 1 further comprising chitosan.

6. The composite material of claim 1, wherein the nitric oxide binding/releasing agent has a formula (1) or (2):

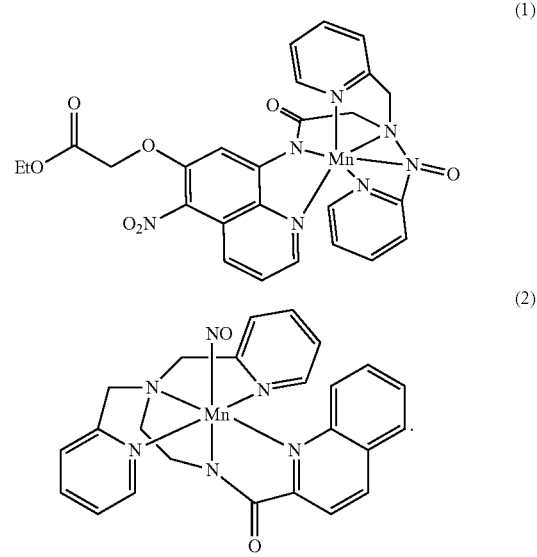

7. The composite material of claim 6, wherein the nitric oxide binding/releasing agent has the formula (1) and the composite material releases nitric oxide when irradiated with near-infrared light having a wavelength of about 650 nm.

8. The composite material of claim 6, wherein the nitric oxide binding/releasing agent has the formula (2) and the composite material releases nitric oxide when irradiated with near-infrared light having a wavelength of about 810 nm.

9. A dressing for a wound comprising the composite material of claim 1.

10. A composite material consisting of:
(a) cellulose;
(b) the nitric oxide binding/releasing agent having the formula (1) or (2);

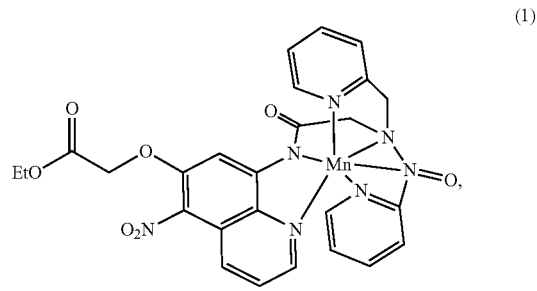

-continued

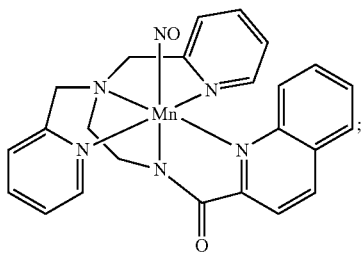

(2)

(c) chitosan and keratin; and (d) ciprofloxacin.

11. The composite material of claim 10, wherein the nitric oxide binding/releasing agent has the formula (1) and the composite material releases nitric oxide when irradiated with near-infrared light having a wavelength of about 650 nm.

12. The composite material of claim 10, wherein the nitric oxide binding/releasing agent has the formula (2) and the composite material releases nitric oxide when irradiated with near-infrared light having a wavelength of about 810 nm.

13. A method for preparing the composite material of claim 1, the method comprising: (a) dissolving the cellulose, the keratin, and the nitric oxide binding/releasing agent in an ionic liquid to form an ionic liquid composition, and (b) removing the ionic liquid from the ionic liquid composition to obtain the composite material.

14. The method of claim 13, further comprising contacting the composite material with nitric oxide after removing the ionic liquid to load the nitric oxide binding/releasing agent with nitric oxide.

15. The method of claim 13, wherein the ionic liquid is removed by steps that include washing the ionic liquid composition with an aqueous solution to obtain the composite material and drying the composite material thus obtained.

16. The method of claim 13, wherein the composite material further comprises metal or metal oxide nanoparticles and the method further comprises dissolving a metal salt in the ionic liquid and forming the metal or metal oxide nanoparticles in the ionic liquid.

17. The method of claim 13, wherein the ionic liquid is an alkylated imidazolium salt selected from a group consisting of 1-butyl-3-methylimidazolium salt, 1-ethyl-3-methylimidazolium salt, and 1-allyl-3-methylimidazolium salt.

18. The method of claim 13, wherein the ionic liquid is 1-butyl-3-methylimidazolium chloride.

19. The method of claim 13, wherein the ionic liquid composition comprises at least 10% w/w of the dissolved cellulose.

20. A method for delivering nitric oxide to a wound, the method comprising: (a) contacting the composite material of claim 1 with a wound, wherein the composite material comprises the nitric oxide binding/releasing agent loaded with nitric oxide; and (b) irradiating the composite material with near-infrared light to release the nitric oxide.

21. The method of claim 20, wherein the near-infrared light has a wavelength between 650 nm and 810 nm.

* * * * *

UNITED STATES PATENT AND TRADEMARK OFFICE
CERTIFICATE OF CORRECTION

PATENT NO. : 11,986,562 B2
APPLICATION NO. : 16/387267
DATED : May 21, 2024
INVENTOR(S) : Chieu D. Tran Page 1 of 1

It is certified that error appears in the above-identified patent and that said Letters Patent is hereby corrected as shown below:

In the Specification

Column 12, Line 37, "03" should be --$O_3$--.

In the Claims

Claim 10, Column 14, Line 52, "the nitric" should be --a nitric--.

Claim 10, Column 14, Line 52, "the formula" should be --a formula--.

Signed and Sealed this
Sixteenth Day of July, 2024

Katherine Kelly Vidal
*Director of the United States Patent and Trademark Office*